(12) United States Patent
Golan et al.

(10) Patent No.: US 11,925,376 B2
(45) Date of Patent: Mar. 12, 2024

(54) METHODS AND DEVICES FOR URETHRAL TREATMENT

(71) Applicant: ProArc Medical Ltd., Misgav Business Park (IL)

(72) Inventors: Shai Golan, Kibbutz Megiddo (IL); Raz Bar-On, Hadera (IL); Boaz Harari, Ganei-Tikva (IL); Yair Feld, Haifa (IL)

(73) Assignee: ProArc Medical Ltd., Misgav Business Park (IL)

( * ) Notice: Subject to any disclaimer, the term of this patent is extended or adjusted under 35 U.S.C. 154(b) by 229 days.

(21) Appl. No.: 17/533,306

(22) Filed: Nov. 23, 2021

(65) Prior Publication Data

US 2022/0104845 A1 Apr. 7, 2022

Related U.S. Application Data

(62) Division of application No. 14/768,766, filed as application No. PCT/IL2014/050281 on Mar. 13, 2014, now abandoned.
(Continued)

(51) Int. Cl.
*A61B 18/14* (2006.01)
*A61B 17/32* (2006.01)
(Continued)

(52) U.S. Cl.
CPC .. *A61B 17/320016* (2013.01); *A61B 18/1492* (2013.01); *A61B 90/39* (2016.02);
(Continued)

(58) Field of Classification Search
CPC ...... A61B 2017/00274; A61B 18/1492; A61B 17/320016
See application file for complete search history.

(56) References Cited

U.S. PATENT DOCUMENTS

| 4,660,560 A | 4/1987 | Klein |
| 5,030,227 A | 7/1991 | Rosenbluth et al. |

(Continued)

FOREIGN PATENT DOCUMENTS

| EP | 0125352 A1 | 11/1984 |
| EP | 1413262 A1 | 4/2004 |

(Continued)

OTHER PUBLICATIONS

Advisory Action for U.S. Appl. No. 13/257,651 dated Nov. 30, 2018.
(Continued)

*Primary Examiner* — Linda C Dvorak
*Assistant Examiner* — Ryan T Clark
(74) *Attorney, Agent, or Firm* — Dorsey & Whitney LLP

(57) ABSTRACT

Apparatus and methods are described for treatment of a urethra that is constricted due to benign prostatic hyperplasia (BPH). A positioning device is used to determine a location of the area of the urethra that is constricted and is to be treated. An execution device includes a dilation balloon, a cutter, an implant carrier, and an implant, the implant and the implant carrier both being disposed outside the outer surface of the dilation balloon. The urethra is dilated by expanding the dilation balloon, and a cut is formed in the inner surface of the urethra using the cutter. The implant is released into the cut within the inner surface of the urethra subsequent to the cutter forming the cut in the inner surface of the urethra, to thereby maintain the urethra in a dilated state. Other embodiments are also described.

15 Claims, 29 Drawing Sheets

Related U.S. Application Data

(60) Provisional application No. 61/783,257, filed on Mar. 14, 2013.

(51) Int. Cl.
*A61B 90/00* (2016.01)
*A61F 2/04* (2013.01)
*A61M 29/00* (2006.01)
*A61B 17/00* (2006.01)
*A61B 18/00* (2006.01)
*A61M 25/04* (2006.01)

(52) U.S. Cl.
CPC ............ *A61F 2/04* (2013.01); *A61M 29/00* (2013.01); *A61B 2017/00274* (2013.01); *A61B 2017/32007* (2017.08); *A61B 2017/320071* (2017.08); *A61B 2017/320082* (2017.08); *A61B 2018/00285* (2013.01); *A61B 2018/00547* (2013.01); *A61B 2018/1412* (2013.01); *A61B 2090/062* (2016.02); *A61F 2002/048* (2013.01); *A61M 25/04* (2013.01)

(56) References Cited

U.S. PATENT DOCUMENTS

| | | | |
|---|---|---|---|
| 5,133,713 | A | 7/1992 | Huang et al. |
| 5,269,802 | A | 12/1993 | Garber |
| 5,643,340 | A | 7/1997 | Nunokawa |
| 5,674,242 | A | 10/1997 | Phan et al. |
| 5,766,203 | A | 6/1998 | Imran et al. |
| 5,921,982 | A | 7/1999 | Lesh et al. |
| 6,070,589 | A | 6/2000 | Keith et al. |
| 6,319,282 | B1 | 11/2001 | Nishi |
| 6,673,101 | B1 | 1/2004 | Fitzgerald et al. |
| 7,004,965 | B2 | 2/2006 | Gross |
| 7,279,002 | B2 * | 10/2007 | Shaw ............... A61L 29/126 623/1.11 |
| 7,632,297 | B2 | 12/2009 | Gross |
| 8,016,845 | B1 | 9/2011 | Sauer |
| 8,145,321 | B2 | 3/2012 | Gross |
| 2002/0007222 | A1 | 1/2002 | Desai |
| 2002/0010489 | A1 | 1/2002 | Grayzel et al. |
| 2002/0032486 | A1 | 3/2002 | Lazarovitz et al. |
| 2002/0032488 | A1 | 3/2002 | Brekke et al. |
| 2002/0035391 | A1 | 3/2002 | Mikus et al. |
| 2003/0055313 | A1 | 3/2003 | Anderson et al. |
| 2003/0060870 | A1 | 3/2003 | Reever |
| 2003/0069467 | A1 | 4/2003 | Lau et al. |
| 2003/0167088 | A1 | 9/2003 | Abraham et al. |
| 2003/0191479 | A1 | 10/2003 | Thornton |
| 2003/0216814 | A1 | 11/2003 | Siegel et al. |
| 2004/0030217 | A1 | 2/2004 | Yeung et al. |
| 2004/0064139 | A1 | 4/2004 | Yossepowitch |
| 2004/0181235 | A1 | 9/2004 | Daignault et al. |
| 2005/0055087 | A1 | 3/2005 | Starksen |
| 2005/0137716 | A1 | 6/2005 | Gross |
| 2006/0095058 | A1 | 5/2006 | Sivan et al. |
| 2006/0149308 | A1 | 7/2006 | Melsheimer et al. |
| 2006/0167540 | A1 | 7/2006 | Masters et al. |
| 2006/0173517 | A1 | 8/2006 | Gross |
| 2006/0229711 | A1 | 10/2006 | Yan et al. |
| 2006/0271151 | A1 | 11/2006 | McGarry et al. |
| 2006/0276871 | A1 | 12/2006 | Lamson et al. |
| 2007/0093781 | A1 | 4/2007 | Kugler et al. |
| 2009/0156977 | A1 | 6/2009 | Daignault et al. |
| 2009/0264987 | A1 | 10/2009 | Gale |
| 2009/0297582 | A1 | 12/2009 | Meyer et al. |
| 2010/0100195 | A1 | 4/2010 | Gross |
| 2010/0130815 | A1 | 5/2010 | Sade et al. |
| 2010/0137893 | A1 | 6/2010 | Kilemnick et al. |
| 2010/0292715 | A1 | 11/2010 | Nering et al. |
| 2010/0312054 | A1 * | 12/2010 | Beyar ............... A61B 18/22 600/108 |
| 2012/0010645 | A1 | 1/2012 | Feld |
| 2013/0268086 | A1 | 10/2013 | Creedon et al. |
| 2014/0012192 | A1 | 1/2014 | Bar-On et al. |
| 2016/0000455 | A1 | 1/2016 | Golan et al. |
| 2016/0096009 | A1 | 4/2016 | Feld |
| 2018/0344995 | A1 | 12/2018 | Bar-On et al. |
| 2019/0381291 | A1 | 12/2019 | Feld |

FOREIGN PATENT DOCUMENTS

| | | |
|---|---|---|
| EP | 1415681 A1 | 5/2004 |
| JP | 2004147812 A | 5/2004 |
| WO | 9404081 A1 | 3/1994 |
| WO | 0143664 A1 | 6/2001 |
| WO | 2007048437 A1 | 5/2007 |
| WO | 2007109621 A2 | 9/2007 |
| WO | 2008056194 A1 | 5/2008 |
| WO | 2008142677 A2 | 11/2008 |
| WO | 2010106543 A2 | 9/2010 |
| WO | 2012123950 A2 | 9/2012 |
| WO | 2014141278 A1 | 9/2014 |
| WO | 2021250588 A1 | 12/2021 |

OTHER PUBLICATIONS

Advisory Action for U.S. Appl. No. 14/005,330 dated Dec. 27, 2017.
Applicant-Initiated Interview Summary for U.S. Appl. No. 13/257,651 dated Jan. 16, 2017.
Applicant-Initiated Interview Summary for U.S. Appl. No. 14/005,330 dated Apr. 28, 2016.
Applicant-Initiated Interview Summary for U.S. Appl. No. 14/005,330 dated Mar. 15, 2017.
Applicant-Initiated Interview Summary for U.S. Appl. No. 14/005,330 dated Nov. 9, 2017.
Applicant-Initiated Interview Summary for U.S. Appl. No. 14/005,330 dated Oct. 6, 2016.
Applicant-Initiated Interview Summary for U.S. Appl. No. 14/768,766 dated Feb. 4, 2019.
Applicant-Initiated Interview Summary for U.S. Appl. No. 14/967,308 dated Feb. 12, 2019.
Communication Pursuant to Article 94(3) EPC for European Application No. 10714484.2 dated Feb. 21, 2017.
Communication Pursuant to Article 94(3) EPC for European Application No. 12716658.5 dated Mar. 23, 2016.
Communication Pursuant to Article 94(3) EPC for European Application No. 12716658.5 dated Sep. 24, 2014.
Communication Pursuant to Article 94(3) EPC for European Application No. 14764625.1 dated Oct. 28, 2019.
Communication Relating to the Results of the Partial International Search for International Application No. PCT/IL2010/000229 dated Nov. 8, 2010.
Communication Relating to the Results of the Partial International Search for International Application No. PCT/IL2012/050094 dated Jul. 4, 2012.
European Search Report and Search Opinion for European Application No. 18215225.6 dated Jan. 17, 2020.
Examiner-Initiated Interview Summary for U.S. Appl. No. 14/005,330 dated Nov. 29, 2016.
Final Office Action for U.S. Appl. No. 13/257,651 dated Apr. 19, 2017.
Final Office Action for U.S. Appl. No. 13/257,651 dated Jul. 16, 2018.
Final Office Action for U.S. Appl. No. 13/257,651 dated Mar. 16, 2015.
Final Office Action for U.S. Appl. No. 13/257,651 dated Mar. 24, 2016.
Final Office Action for U.S. Appl. No. 14/005,330 dated Aug. 18, 2017.
Final Office Action for U.S. Appl. No. 14/005,330 dated Aug. 24, 2016.
Final Office Action for U.S. Appl. No. 14/768,766 dated Apr. 2, 2021.

(56) References Cited

OTHER PUBLICATIONS

Final Office Action for U.S. Appl. No. 14/768,766 dated Aug. 23, 2021.
Final Office Action for U.S. Appl. No. 14/768,766 dated Jul. 29, 2019.
Final Office Action for U.S. Appl. No. 14/967,308 dated Dec. 13, 2018.
International Preliminary Report on Patentability for International Application No. PCT/IL2010/000229 dated Sep. 29, 2011.
International Preliminary Report on Patentability for International Application No. PCT/IL2012/050094 dated Sep. 26, 2013.
International Preliminary Report on Patentability for International Application No. PCT/IL2014/050281 dated Sep. 24, 2015.
International Search Report and Written Opinion from International Application No. PCT/IL2010/000229 dated Jan. 18, 2011.
International Search Report and Written Opinion from International Application No. PCT/IL2012/050094 dated Sep. 13, 2012.
International Search Report and Written Opinion from International Application No. PCT/IL2014/050281 dated Jul. 3, 2014.
Non-Final Office Action for U.S. Appl. No. 13/257,651 dated Aug. 12, 2014.
Non-Final Office Action for U.S. Appl. No. 13/257,651 dated Sep. 15, 2015.
Non-Final Office Action for U.S. Appl. No. 13/257,651 dated Sep. 8, 2017.
Non-Final Office Action for U.S. Appl. No. 13/257,651 dated Sep. 9, 2016.
Non-Final Office Action for U.S. Appl. No. 14/005,330 dated Feb. 16, 2016.
Non-Final Office Action for U.S. Appl. No. 14/005,330 dated Mar. 1, 2017.
Non-Final Office Action for U.S. Appl. No. 14/768,766 dated Jul. 22, 2020.
Non-Final Office Action for U.S. Appl. No. 14/768,766 dated Nov. 19, 2018.
Non-Final Office Action for U.S. Appl. No. 14/967,308 dated Mar. 28, 2018.
Rectification of Obvious Mistake Under Rule 91.1. for International Application No. PCT/1L2010/000229 dated Jul. 6, 2010.
Requisition by Examiner from the Innovation, Science and Economic Development Canada for Canadian Application No. 2,938,823 dated Apr. 3, 2020.
Restriction Requirement for U.S. Appl. No. 13/257,651 dated Apr. 22, 2014.
Restriction Requirement for U.S. Appl. No. 14/005,330 dated Jul. 14, 2015.
Restriction Requirement for U.S. Appl. No. 14/768,766 dated Apr. 20, 2018.
Restriction Requirement for U.S. Appl. No. 14/967,308 dated Nov. 30, 2017.
Supplementary European Search Report and the European Search Opinion for European Application No. 14764625.1 dated Oct. 28, 2016.
U.S. Appl. No. 14/768,766, filed Aug. 19, 2015.
International Search Report and Written Opinion from International Application No. PCTIB2021055063 dated Aug. 10, 2021.
Non-Final Office Action for U.S. Appl. No. 16/048,481 dated Mar. 11, 2022.
Non-Final Office Action for U.S. Appl. No. 16/554,774 dated Jun. 8, 2022.
Restriction Requirement for U.S. Appl. No. 16/554,774 dated Feb. 4, 2022.
U.S. Appl. No. 17/533,306, filed Nov. 23, 2021.
Final Office Action for U.S. Appl. No. 16/048,481 dated Nov. 6, 2023.
Non-Final Office Action for U.S. Appl. No. 16/048,481 dated Nov. 2, 2023.
Examination Report for European Application No. 18215225.6 dated Nov. 2, 2023.

\* cited by examiner

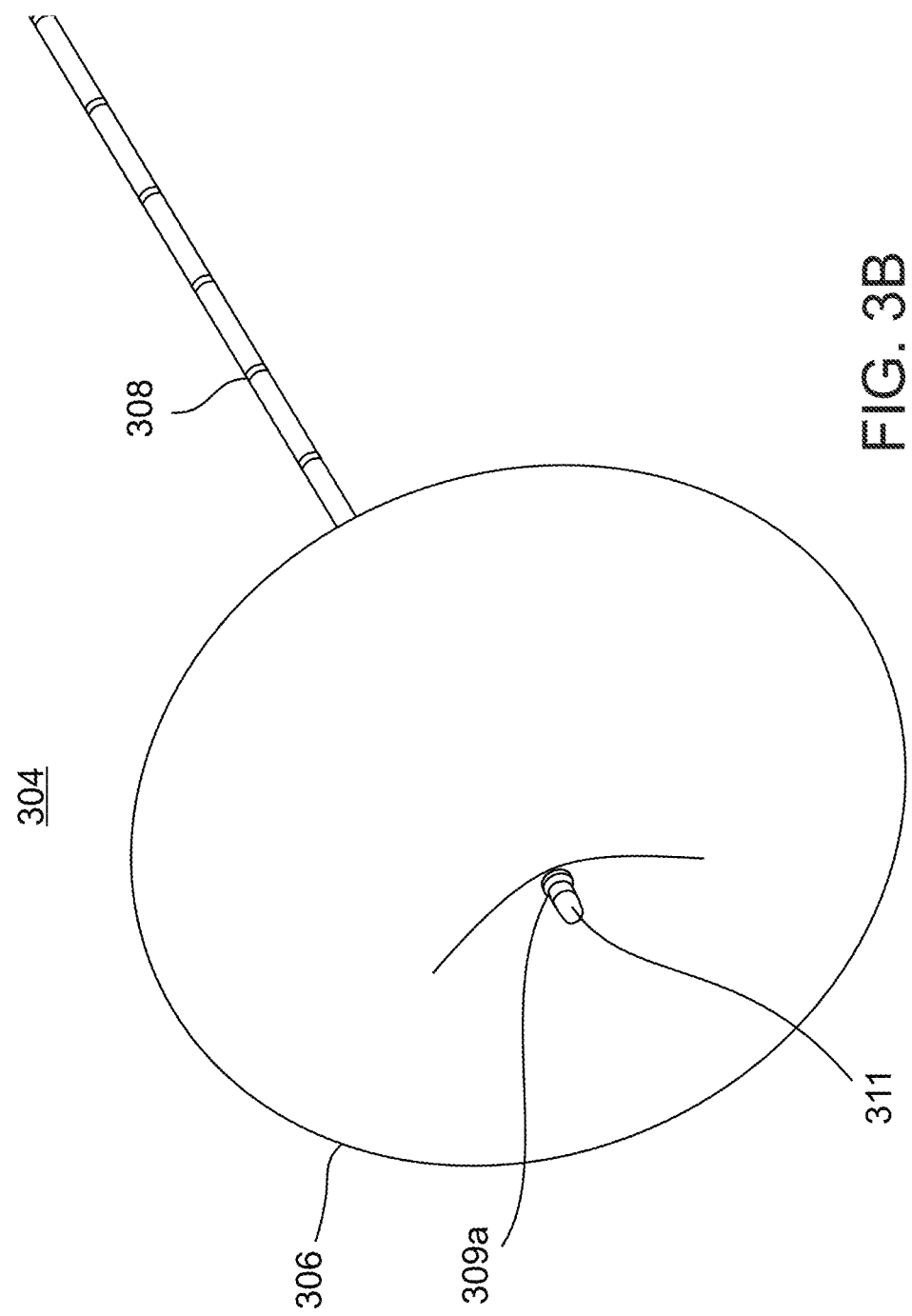

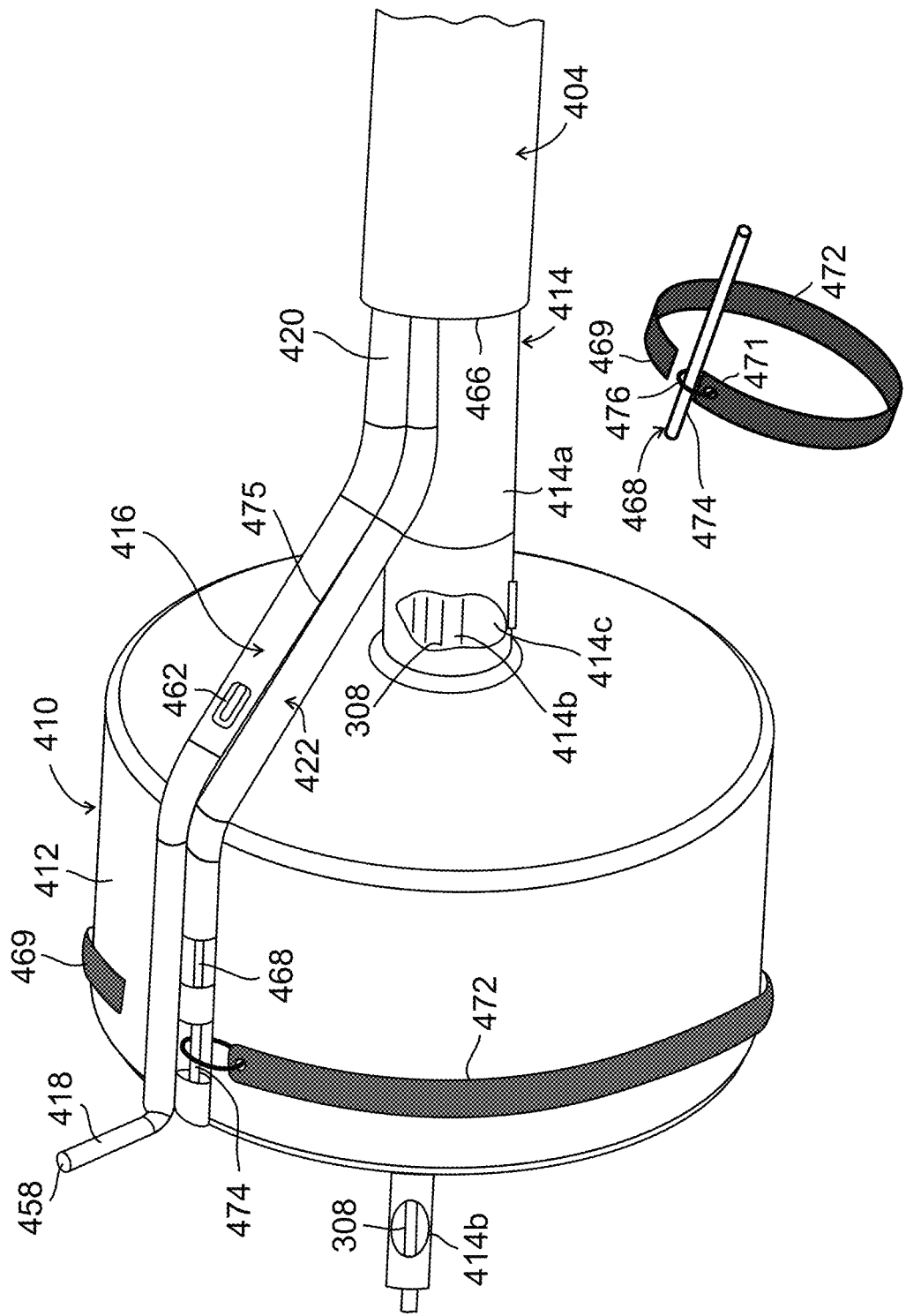

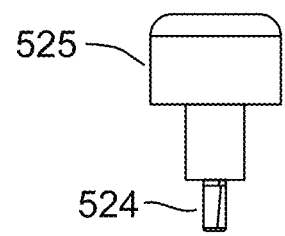
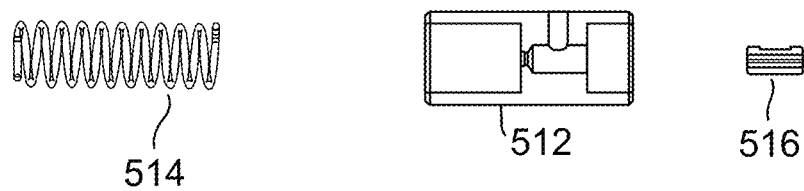
FIG. 5D

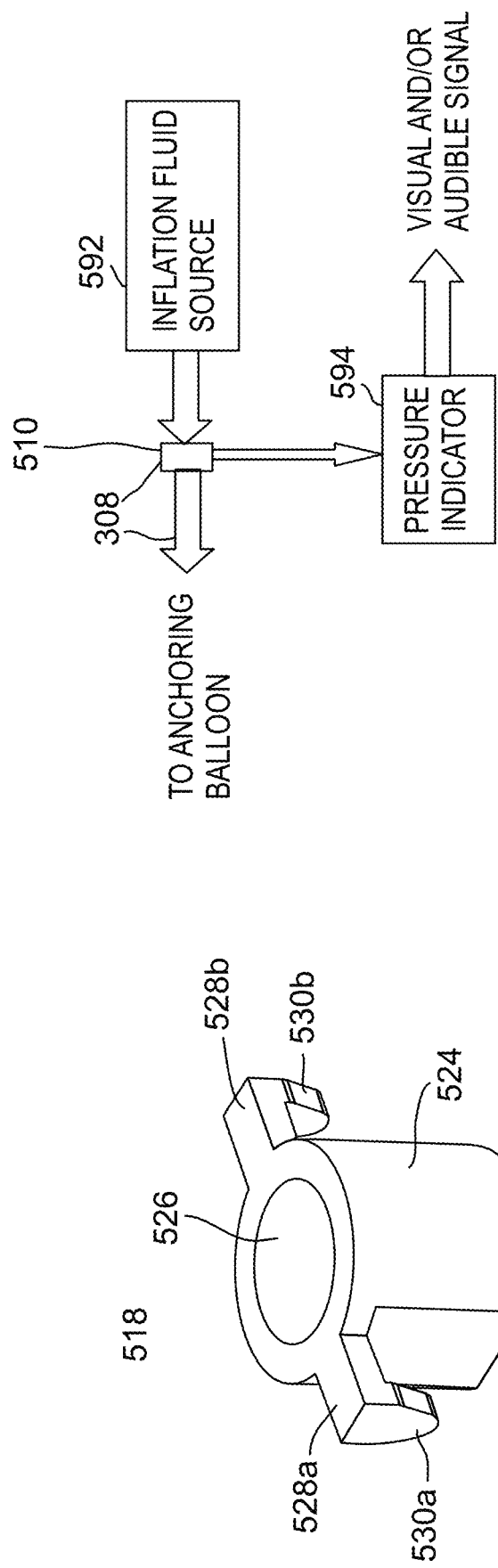

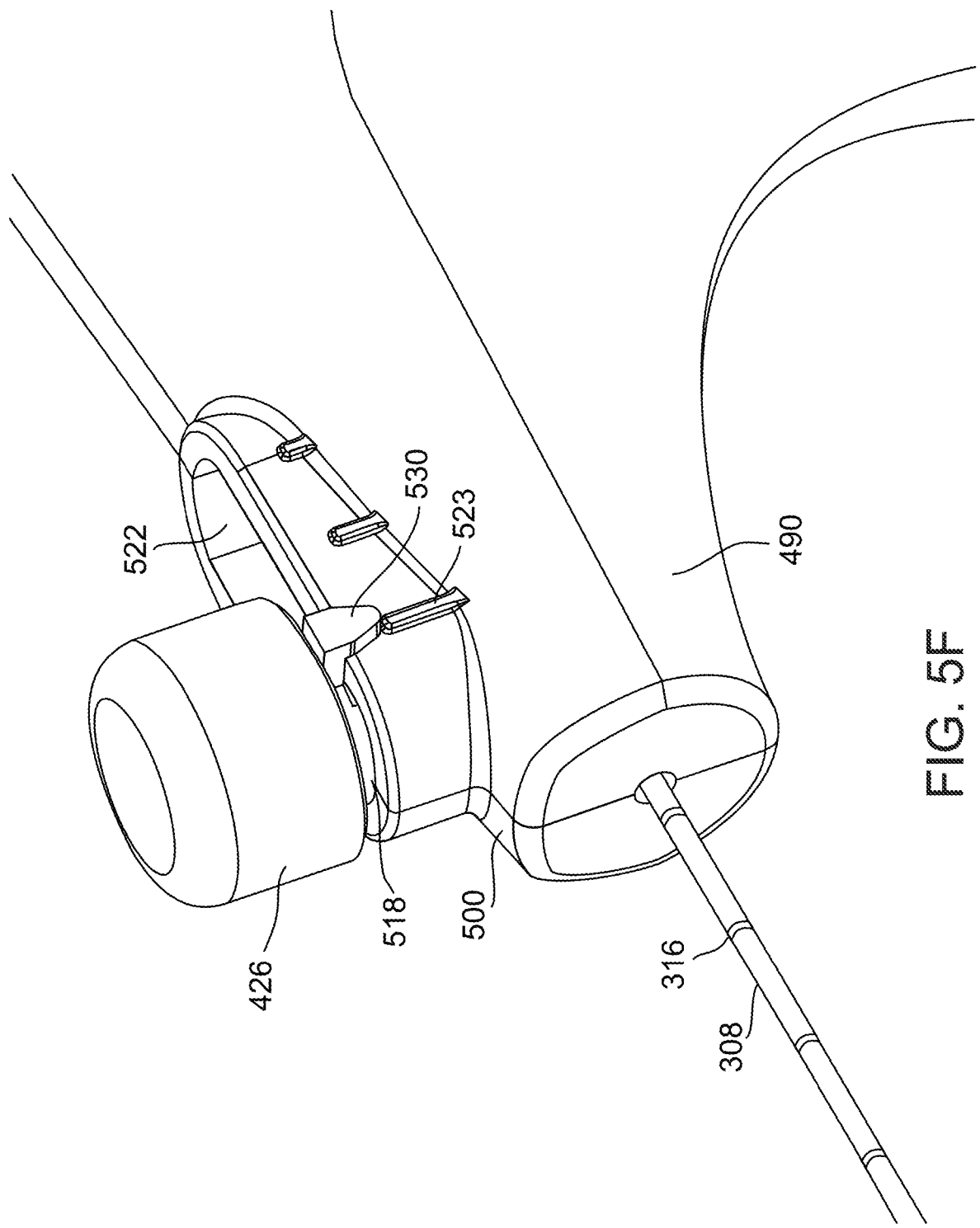

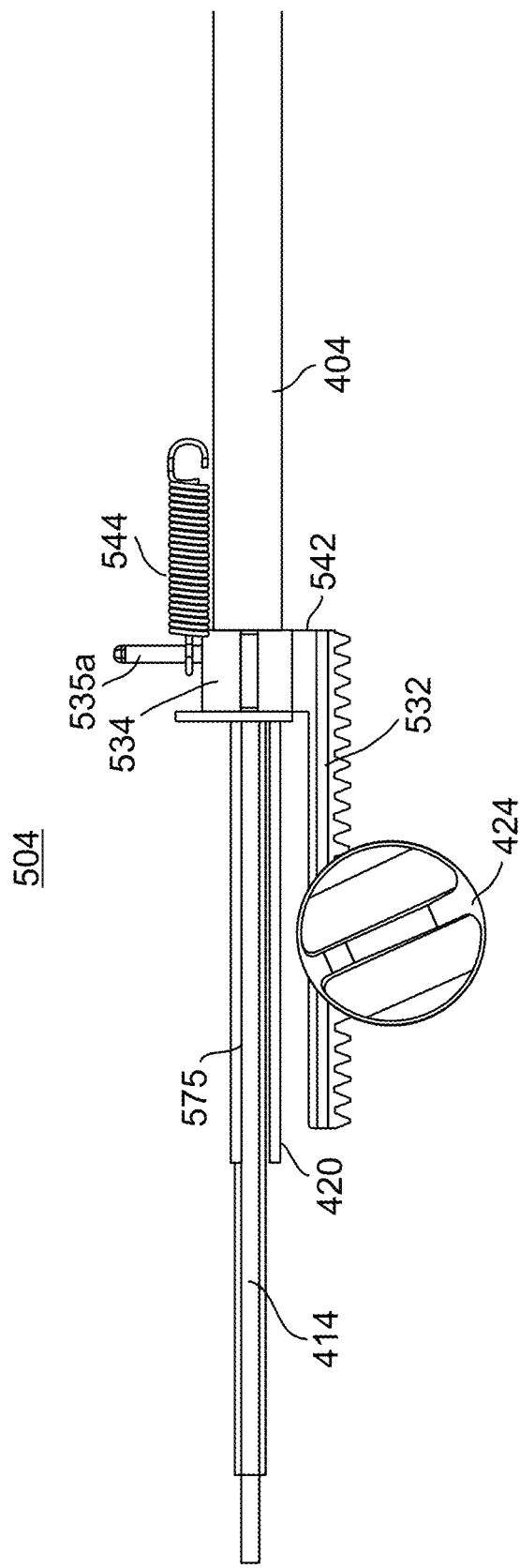

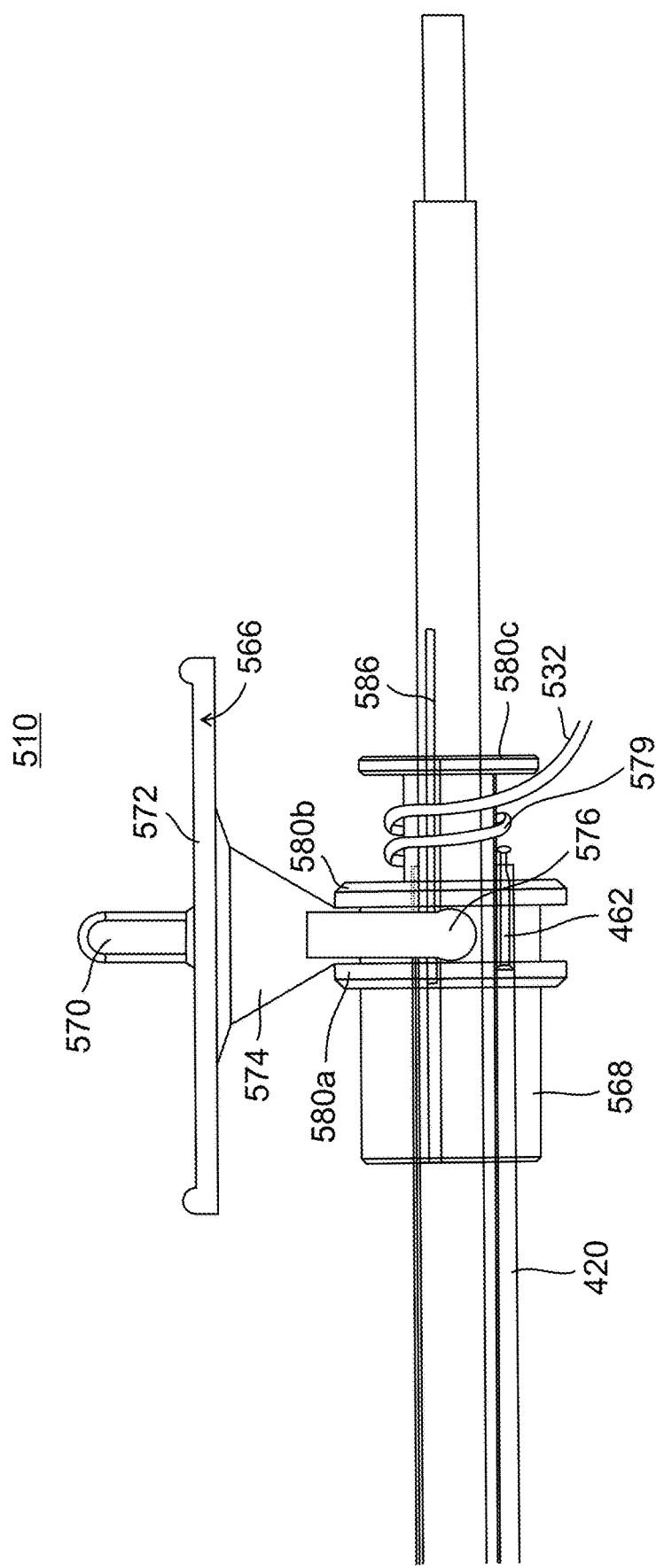

1

METHODS AND DEVICES FOR URETHRAL TREATMENT

RELATED APPLICATIONS

The present application is a divisional of U.S. Ser. No. 14/768,766 to Golan filed on Aug. 19, 2015, which is the US National Phase of PCT Patent Application No. PCT/IL2014/050281, published as WO2014/141278, having International filing date of Mar. 13, 2014, which claims the priority from U.S. Provisional Patent Application No. 61/783,257 filed on Mar. 14, 2013.

This application is related to commonly owned International Application IL 2010/000229, filed on Mar. 21, 2010, and published as WO/2010/106543 (herein referred to as the '229 application), and to International Application IL2012/050094, filed on Mar. 15, 2012, and published as WO2012/123950 (herein referred to as the '094 application"). The content of the '229 and '094 applications are incorporated by reference as if fully set forth herein in their entirety.

FIELD OF THE INVENTION

The present invention, in some embodiments thereof, relates to systems and methods for treatment of intra-body lumens, and, more particularly, but not exclusively, to methods and devices for dilating and/or assisting in dilation and/or maintaining dilation of the urethra to relieve obstruction resulting, for example from benign prostatic hyperplasia (BPH).

Benign Prostatic Hypertrophy (BPH)

It is common for the prostate gland to become enlarged as a man ages. As a male matures, the prostate goes through two main periods of growth, first early in puberty, and then again at around age 25, when the growth begins again, and continues on through life. One of the effects of this continued growth can be pressure on the urethra, the passage through which urine passes from the bladder and the penis.

The urethra is surrounded by the prostate for part of its length. Within the confines of the prostate, the urine flows through a passage having a generally triangular cross-section. As the prostate enlarges, the layer of tissue surrounding the prostate restricts the prostate from expanding outward, causing the prostate to constrict the urethral passage. The condition of an enlarged, non-cancerous prostate is called benign prostatic hyperplasia (BPH).

Though the prostate continues to grow during most of a man's life, BPH rarely causes symptoms before age 40, but more than half of men in their sixties and as many as 90 percent in their seventies and eighties have some symptoms. BPH can make it difficult to completely empty the bladder and is associated with other urinary system problems well known in the medical field.

Current Treatment Techniques

Men who have symptoms associated with BPH usually need some kind of treatment at some time. Although the need for treatment is not usually urgent, doctors generally advise treatment once the problems become bothersome or present a health risk.

The most commonly used treatments for BPH include drug therapy, minimally invasive mechanical treatment, and surgery.

Among the drugs approved, for example, by the U.S. FDA, are Finasteride (Proscar), dutasteride (Avodart), terazosin (Hytrin), doxazosin (Cardura), tamsulosin (Flomax), and alfuzosin (Uroxatral). These drugs act by relaxing the smooth muscle of the prostate and bladder neck to improve urine flow and to reduce bladder outlet obstruction. Use of finasteride and doxazosin together has also been found to be more effective than using either drug alone.

Drug treatment may only be partially effective in some cases. Researchers have therefore developed several mechanical procedures that relieve BPH symptoms but are less invasive than conventional surgery. These include transurethral microwave thermotherapy (TUMT), which uses microwaves to heat and destroy portions of prostate tissue, transurethral needle ablation (TUNA), which employs low-level radio-frequency energy delivered through twin needles to burn away selected regions of the enlarged prostate, and water-induced thermotherapy, which uses heated water to destroy portions of prostate tissue. The use of ultrasound waves to destroy prostate tissue is also undergoing clinical trials in the United States.

Urethral stents have also been employed in some instances, with varying degrees of effectiveness.

Surgical removal of part of the prostate, thereby reducing pressure against the urethra is often regarded as the best long-term solution for patients with BPH. Among the types of surgery commonly employed is transurethral surgery which requires no external incision. Such procedures include transurethral resection of the prostate (TURP), by which prostate tissue is removed, transurethral incision of the prostate (TUIP), by which the urethra is widened by making a few small cuts in the bladder neck where the urethra joins the bladder, and in the prostate gland itself, and laser induced prostate tissue removal.

In the few cases where transurethral surgical procedures are not indicated, open surgery, which requires an external incision, may be used.

The previously mentioned '229 International Application teaches dilating a constricted urethra by use of a balloon catheter or other expandable dilation unit and implanting a C-shaped or ring-like open loop into a cut formed in the inner surface of the prostate surrounding the urethra within the constricted area to maintain the dilation. Other relevant prior art includes U.S. Pat. Nos. 7,004,965, 8,145,321, and 7,632,297, and Published U.S. patent applications 2006/0173517, 2005/0137716, 2010/0100195, and 2010/0130815.

SUMMARY OF THE INVENTION

According to an aspect of some embodiments of the invention, there is provided a system for treatment of a constricted intrabody lumen comprising a planning device for performing a planning stage of the treatment including an anchoring unit, and a set of reference markers configured for identifying one or more areas for treatment, and a device for executing the treatment including a dilation unit including an expandable element to enlarge the lumen in the area to be treated, an implant carrier releasably connectable to an implant for delivery to the area to be treated, and a cutter including a blade positionable to form a cut in the inner surface of the tissue surrounding the area to be treated to receive the implant.

Optionally, the reference markers are configured so that treatment areas can be visually identified using an optical device inserted in the lumen.

Optionally, the lumen is a urethra that is constricted due to BPH and the anchoring element is shaped and sized to lodge in the neck of a bladder.

Optionally, the anchoring unit includes an expandable anchoring element and a delivery element configured to expand the anchoring element. Optionally, in some embodiments, the reference markers are carried near the distal end of the delivery element for the anchoring element. Optionally, the anchoring element is a balloon that is substantially toroidal in shape upon inflation, and the delivery element is a shaft including a fluid passage connectable to a source of inflation fluid. Optionally, the dilation unit delivery element is comprised of two concentric tubes partially attached together at least distally, and the fluid path is defined by a substantially annular passage between the two tubes.

Optionally, according to some embodiments, the anchoring element and/or the dilation element is self-expanding, and a delivery shaft is provided to release the respective self-expanding element for expansion.

According to some embodiments, the cutter is comprised of an implant carrier portion configured to engage releasably with an implant, and the execution device further comprises a release unit to separate the implant from the carrier portion of the cutter.

According to some embodiments, the implant carrier is comprised of an elongated pin that includes a projection at its distal end to which an implant is releasably attachable for delivery. Optionally, the pin is coupled to an actuator configured to pull the pin proximally to disconnect the implant from the projection. Optionally, the projection is sized and positioned to engage a hole or a loop at one end of an implant.

According to some embodiments, the cutter is rotatable, and the cutter blade is comprised of a proximal portion and a distal portion separated by a resilient hinge area; so that the blade assumes a generally L-shaped operating configuration with its distal end in contact with the surface of the tissue surrounding the lumen to form a cut as the cutter is rotated.

According to some embodiments, the cutter blade is delivered to the treatment area in a retractable outer sheath which also carries the dilation unit and the implant carrier and release mechanism, and the blade is in a delivery configuration in the outer sheath and blade assumes its L-shaped operating configuration when the outer sheath is retracted.

According to some embodiments, the cutter includes a delivery tube for the blade and a pusher wire coupled to the proximal end of the blade to push it distally out of its delivery tube so that it assumes its operating configuration and to pull the blade proximally to retract the blade back into the delivery tube for withdrawal of the execution device from the lumen. According to some embodiments, the pusher wire is connectable to a diathermy machine or a piezoelectric transducer to provide electric or electromechanical energy to form the cut for the implant.

According to some embodiments, there is provided a mechanism operable to retract the cutter delivery tube proximally from the blade so the blade emerges from the delivery tube and assumes its operating configuration, and to extend the delivery tube distally so that the blade is received back within the delivery tube for withdrawal of the execution device from the lumen.

According to an aspect of some embodiments of the invention, various parts of the system are interchangeable. In some embodiments, an operating handle configured for connection to both the planning and execution stage devices.

According to some embodiments, separate operating handles provided for connection to the planning and execution stage devices to control the functions of the respective stages.

According to some embodiments, the planning stage device anchoring unit is configured to be separated from its operating handle and coupled to the execution stage device during the execution stage. Optionally, the execution device includes a dedicated anchoring unit. Optionally, the execution stage anchoring unit includes a set of position reference markers at a proximal end thereof positionally correlated with the set of reference markers at the distal end of the planning stage anchoring unit.

According to some embodiments, the planning and execution devices are integrated in a single unit.

According to some embodiments, the planning device includes a second set of reference markers at a proximal end of the anchoring element delivery element positionally correlated with the set of markers at the distal end of the delivery tube, relative to which the deployment locations identified during the planning stage are located during the execution stage.

According to some embodiments, a tensioning mechanism is provided for applying a selectable and repeatable proximally directed force to the anchoring element. Optionally, the tensioning mechanism is comprised in an operating handle for the planning stage device, and the planning stage operating handle is connectable to the execution stage device. Optionally, the planning and execution stage devices each include separate dedicated tensioning mechanisms in operating handles for the respective devices.

Optionally, the tensioning mechanism comprises a compression spring, a guide element on which an actuator for the tensioning mechanism is moveably mounted, and a locking element that connects the guide element to a delivery tube for the anchoring element so that a proximally directed force applied to the tensioning mechanism is transferred to the anchoring element delivery element.

According to some embodiments, the dilation unit is comprised of a plurality of longitudinally extending balloons disposed in a generally circular pattern.

According to some embodiments, the dilation unit is rotatable and the implant carrier, the implant release mechanism, and the cutter are coupled to the dilation unit and are rotatable thereby. Optionally, the execution device further includes a rotation mechanism for manually rotating the dilation unit. Alternatively, the rotation mechanism is motor-operated.

According to an aspect of some embodiments of the invention, the system provides the capability for delivering deploying multiple implants. According to some embodiments, the implant carrier is configured to deliver a plurality of implants simultaneously, and to release the implants simultaneously or one at a time.

According some embodiments, cutter includes a plurality of axially spaced blades configured to form a plurality of cuts simultaneously or one at a time.

An aspect of some embodiments of the invention relates to the construction of an operating handle for the execution stage device. According to some embodiments, the operating handle includes a mechanism configured to retract an outer sheath, a mechanism configured to rotate a cutter, a mechanism configured to provide fluid-tight delivery of inflation fluid to a rotatable delivery element for a dilation element, a mechanism configured to release an implant from a carrier; and a mechanism configured to push an implant out of the outer sheath.

According to some embodiments, a tensioning mechanism is provided to apply proximally directed force to an anchoring balloon element for the system. Optionally, there is also provided a pressure sensor connectable to an inflation tube for the anchoring balloon; and a pressure indicator that is responsive to an increase of the pressure in the anchoring element inflation tube when tension is applied during the planning stage to provide a visual and/or aural indication when the same tension is applied during the execution stage. Optionally, there is also provided a holder for the execution stage operating handle attachable to a surgical table that maintains tension applied during the execution stage without human intervention.

According to some embodiments, wherein the dilation unit is rotatable, there is provided an inflation port configured to provide inflation fluid for the dilation balloon while the dilation unit rotates. Optionally, the inflation port comprises a body, a tubular passage, one end of which is coupled to the body, and the other end terminates in a fitting connectable to a source of inflation fluid, end sections on proximal and distal ends of the body including portions formed of a resilient material, that provide fluid-tight rotatable seal for the dilation unit inflation tube.

An aspect of some embodiments, relates to a method for treating a bodily lumen comprising identifying one or more areas of the lumen requiring treatment during a planning stage using a planning device inserted in the lumen, delivering an implant in a compressed condition for deployment at the treatment area, expanding the lumen in the treatment area, forming a cut in the inner surface of the tissue surrounding the constricted area, and inserting an implant into the cut to maintain the expansion of the lumen According to some embodiments, delivery of the implant, expanding the lumen, forming the cut, and inserting the implant into the cut are performed using an execution device inserted into the lumen after an area requiring treatment has been identified.

Optionally, forming the cut includes connecting a cutter comprised in the execution device to a diathermy machine or a piezoelectric transducer to provide a source of electrical or electromechanical energy. Optionally, the cut is formed by rotating the cutter around an inner surface of the tissue surrounding an area of the lumen requiring treatment.

According to some embodiments, the implant is removed after a predetermined time. Alternatively, the implants are formed of a material that is biodegradable.

According to some embodiments, the lumen to be treated is a urethra constricted due to BPH, and the implant is deployed in the inner surface of the prostate defining the portion of the urethra within the prostate. Optionally, the implant is an open generally C-shaped ring. Optionally, for treatment of BPH, the implant is released for deployment with its open side facing toward the rectum wall.

According to some embodiments, the planning stage includes anchoring the planning device at a desired location in the lumen using an expandable anchoring element. Optionally, desired deployment locations are identified visually during the planning stage relative to a first set of position reference markers comprised in the positioning unit, using an optical device inserted into the lumen and the identified deployment locations are determined during the execution stage relative to a second set of position reference markers visible outside the lumen and positionally correlated with the first set of position reference markers.

According to some embodiments, the anchoring and dilation elements are balloons, and are inflated using a liquid as an inflation fluid.

According to some embodiments, the positioning unit remains in the lumen after completion of the planning stage; and is connected to the positioning unit to the execution device for use during the execution stage.

According to some embodiments, two or more implants are delivered to the area to be treated simultaneously, the cuts are formed for all of the implants simultaneously, and all the implants are deployed simultaneously.

Optionally, two or more implants are delivered simultaneously using a single unit for delivery of all the implants. Alternatively, or each implant is delivered by a separate device, and further comprising forming cuts for the implants at the time the respective implants are delivered.

According to some embodiments, tension is applied to lodge an anchoring balloon firmly in the neck of the bladder during the planning and execution stages for treatment of BPH.

According to some embodiments, tension is applied during the execution stage is selected in reference to visible markers on an operating handle for the execution stage device or according to an audible or visual signal provided by a pressure indicator according to tension applied during the planning stage. Optionally, the execution stage device is attached to a holder on a surgical table to maintain tension applied during the execution stage.

Optionally according to some embodiments, the cut is formed by a cutter delivered to the implantation site, or by the implant, or by cooperation of a cutter and the implant.

Optionally, according to some embodiments, the implant-receiving cut is closed after deployment of the implant by application of an adhesive, or by a clamp, or by a suture.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods, and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 3B is an enlarged perspective view of an anchoring element for the device of FIG. 3A according to some embodiments;

FIG. 4B is an enlarged side perspective of the distal end of the execution stage device shown in FIG. 4A according to some embodiments;

FIG. 4C is an enlarged side perspective view of an exemplary implant and an implant release mechanism according to some embodiments;

FIG. 5D is an exploded view of the tensioning mechanism shown in FIG. 5C;

FIG. 5E is a perspective view of a marker element comprised in the tensioning mechanism shown in FIGS. 5A through 5D according to some embodiments;

FIG. 5F is an enlarged perspective view showing the manner in which the marker element shown in FIG. 5E cooperates with tensioning markers on the execution stage operating handle;

FIG. 5G is a schematic block diagram of an alternative way of indicating tension according to some embodiments;

FIG. 5H is a side elevation of an exemplary outer sheath retraction mechanism for the operating stage device according to some embodiments;

FIG. 5K is a side elevation view of an implant release trigger mechanism comprised in the execution stage device according to some embodiments;

FIG. 5O is a perspective view of the implant pusher shown in FIG. 5N;

DETAILED DESCRIPTION OF THE INVENTION

Figure 1A:
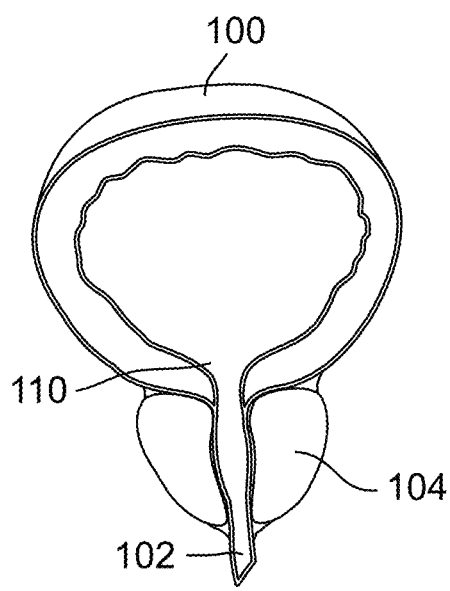
FIG. 1A is an illustration of a bladder, a normal prostate and a part of a urethra.

Preliminary Clarification Regarding the Terms "Distal" and "Proximal"

Preliminarily, for purposes of clarity, it should be noted that the terms "proximal" and "distal" which are used herein are conventionally defined relative to a point of reference. For example, when the urethra is constricted in more than one location, the constriction closest to the bladder would generally be referred to as "proximal" to the bladder" and the constriction furthest from the bladder will be referred to as "distal". On the other hand, with reference to a surgical apparatus, the directions are usually referred to in the opposite way so that the part closest to the surgeon is considered the proximal end while the opposite end is regarded as the distal end. The reference point will be stated when either term is used herein if not completely clear from the context.

Introductory Overview

The present invention, in some embodiments thereof, relates to systems and methods for treatment of intra-body lumens. By way of a non-limiting example, some embodiments relate specifically to systems and methods for dilating and/or assisting in dilation and/or maintaining dilation of the urethra to relieve obstruction resulting, for example, from benign prostatic hyperplasia (BPH).

Broadly stated, the systems and methods are designed to implement a two-stage procedure comprised of a planning stage during which an area or areas to be treated are identified, and an execution stage during which the lumen is dilated, and one or more implants are deployed to help maintain the patency of the dilated lumen.

To this end, an aspect of some embodiments of the invention relates to the construction of a device for implementing the planning stage, In some embodiments, the planning stage device includes a set of reference markers relative to which one or more areas for treatment can be identified, optionally, the planning device includes an anchoring unit formed of an anchoring element, and a delivery element for the anchoring element. Optionally, the anchoring element is a balloon and the delivery element provides a fluid path for inflation fluid. Optionally, the inflated anchoring balloon is toroidally shaped after it is inflated.

Optionally the anchoring element is self-expanding and the delivery element is configured to release the anchoring element (for example, from a sheath) for expansion.

Optionally, the reference markers are carried by the delivery element for the anchoring element.

An aspect of some embodiments of the invention relates to the construction of a device for implementing the execution stage.

In some embodiments, the execution device includes a dilation unit to enlarge the lumen in an area to be treated, a carrier to releasably deliver an implant to the area to be treated, and a cutter including a blade positionable to form a cut in the inner surface of the tissue surrounding the area to be treated.

Optionally, the dilation unit includes an expandable element and a delivery element for the expandable element. Optionally, the expandable element is a balloon and the delivery element provides a fluid path for inflating the balloon. Optionally, the dilation balloon delivery element is comprised of two concentric tubes partially attached together at least distally, and the fluid path is defined by a substantially annular passage between the two tubes.

Optionally, the expandable element is self-expanding, and the delivery element is constructed to release the expandable element (for example, from a sheath) so it can expand.

According to some embodiments, the cutter includes a portion configured to deliver the implant. Optionally the implant carrier portion of the cutter is a projection, for example, a pin, extending from the cutter blade, configured to engage releasably with a complementary portion of an implant. Optionally, the complementary portion of the implant is a hole. Optionally, it is a wire loop. Optionally, in such embodiments, a release mechanism is provided as part of the execution device to separate the implant from the carrier portion of the cutter.

According to some embodiments, delivery and release of the implant is provided for by an integrated carrier and release mechanism. Optionally, in such embodiments, the implant is attached to a projection at a distal end of a release pin for delivery. Optionally, the projection extends through a hole at one end of the implant. Optionally, the projection extends though a loop attached at the end of the implant.

Optionally, the pin extends to a release mechanism, for example, in an operating handle for the execution device. Optionally, the release mechanism is operable to retract the pin proximately to separate it from the implant.

Optionally, a release mechanism as just described may be employed in embodiments of the invention in which the implant is carried by the cutter.

Optionally, in embodiments employing a unitary implant and release mechanism and in embodiments in which the implant is delivered by the cutter, the release mechanism may be configured to retract the cutter blade proximally when the release pin is pulled proximally.

An aspect of the invention relates to the construction of the cutter and the cutter blade. According to some embodiments, one or more of the features described below may be incorporated in cutters comprised in systems according to the invention:

(a) the cutter is rotatable;
(b) the cutter blade is comprised of a proximal portion and a distal portion separated by a resilient hinge area;
(c) the cutter is configured so that the distal portion of the blade is delivered to a treatment site folded proximally along the proximal portion, and is releasable to so it assumes a generally L-shaped operating configuration with its distal end in contact with the surface of the tissue surrounding the lumen to form a cut as the cutter is rotated;
(d) a delivery tube for the blade and a pusher wire configured to engage the proximal end of the blade to push it distally out of its delivery tube so that it assumes its operating configuration and to pull the blade proximally to retract the blade back into the delivery tube for withdrawal of the execution device from the lumen;
(e) A delivery tube for the blade and a mechanism operable to retract the cutter delivery tube proximally from the blade so the blade emerges from the delivery tube and assumes its operating configuration, and to extend the delivery tube distally so that the blade is received back within the delivery tube for withdrawal of the execution device from the lumen;
(f) the cutter is connectable to a source of electric or electromechanical energy to form the cut for the implant;
(g) the source of energy is a diathermy machine or a piezoelectric transducer;
(h) the blade is formed of a resilient material;
(i) a hinge is formed in an area between the proximal and a distal parts by heat-treating the area;
(j) the blade is folded at the hinge area in the tube during delivery to the treatment area;
(k) the blade is delivered in an outer sheath along with an implant carrier and release mechanism and a dilation unit in a delivery configuration in which the distal part of the blade is bent distally, for example, at an angle in the range of about 45 to about 90 degrees distally relative to the direction corresponding to its cutting configuration, so that when the outer sheath is retracted, the distal part of the blade assumes its cutting configuration;
(l) the distal part of the cutter blade is of sufficient width in a direction tangential to the cutting direction that it does not deform while the cut is being made;
(m) the thickness of the distal part of the cutter blade in a longitudinal direction of the lumen is sufficient to accommodate the width of the implant, but not so thick as to interfere with it being folded for release from the lumen;
(n) the length of the distal part of the blade is sufficient for formation of a cut within which the implant can be fully seated.

An aspect of some embodiments of the invention pertains to interchangeability of certain parts of the planning and execution stage devices. In some such embodiments, a single operating handle is configured for connection to both the planning and execution stage devices to control their respective functions. Alternatively, separate operating handles are provided for the planning and execution stage devices.

In some embodiments, the planning stage device anchoring unit is configured to be separated from its operating handle and coupled to the execution stage device during the execution stage. Alternatively, the execution device includes a dedicated anchoring unit. Optionally, the execution stage anchoring unit includes a set of position reference markers at a proximal end correlated with the set of reference markers at the distal end of the planning stage anchoring unit.

In some embodiments, the planning and execution devices are integrated in a single unit.

In embodiments for which the anchoring unit is coupled to the execution device during the execution stage, there is provided a second set of reference markers are at the proximal end of the anchoring element delivery element that are positionally correlated with the set of markers at the distal end.

In some embodiments, the planning stage device and the execution stage device each includes a tensioning mechanism for applying a selectable and repeatable proximally directed force to the anchoring element. Optionally, the execution device does not include a dedicated tensioning mechanism. In such embodiments, a tensioning mechanism for the execution device is provided by connecting an operating handle for the planning device to an operating handle for the execution device.

In some embodiments, the tensioning mechanism(s) are comprised in an operating handle. Optionally, the tensioning mechanism(s) include one or more of the following features:

(a) a compression spring;
(b) a guide element on which an actuator for the tensioning mechanism actuator is moveably mounted;

(c) a locking element inside the guide element that connects the guide element to a delivery tube for a delivery element for an anchoring element;

(d) a locking screw that passes through a passage in the guide element and immobilizes the anchoring element delivery element relative to the guide element when the locking screw is sufficiently tightened and releases the delivery element when the screw is sufficiently loosened;

(e) the locking element is a resilient tube-like structure, for example a cylinder formed of a resilient material with a longitudinal slit so that it can be compressed by the locking screw;

(f) the inner tube of the dilation balloon inflation element is sized and configured to receive the anchoring element delivery element therein.

According to some embodiments, one or more of the following features may also be included in an operating handle for the execution device:

(a) the dilation unit is comprised of a plurality of longitudinally extending balloons disposed in a generally circular pattern and a delivery element for the balloons that includes a fluid passage connectable at its proximal end to a source of inflation fluid to inflate the dilation balloons;

(b) the dilation unit, the implant carrier and release arrangement, and the cutter are delivered to the treatment site in a retractable outer sheath;

(c) the dilation unit is rotatable and the implant carrier, the implant release mechanism, and the cutter are rotatable thereby;

(d) the implant carrier is configured to deliver a plurality of implants simultaneously, and to release the implants simultaneously or one at a the same time;

(e) the cutter includes a plurality of axially spaced blades configured to form a plurality of cuts simultaneously or one at a time;

(f) a mechanism configured to retract an outer sheath;

(g) a mechanism configured to release a cutter blade to an operating position;

(h) a mechanism configured to provide fluid-tight delivery of inflation fluid to a rotatable delivery element for a dilation element;

(i) a mechanism configured to release an implant from a carrier for deployment;

(j) a mechanism configured to push an implant out of the outer sheath;

(k) a pressure sensor connectable to an anchoring element inflation tube for an anchoring balloon and a pressure indicator, the pressure indicator being responsive to an increase of the pressure in the anchoring element inflation tube when tension is applied during the planning stage to provide a visual and/or aural indication when the same tension is applied during the execution stage;

(l) a holder for the execution stage operating handle attachable to a surgical table that maintains tension applied during the execution stage without human intervention;

(m) an inflation port configured to provide inflation fluid for the dilation balloon while the dilation unit rotates.

In some embodiments, feature (i) above optionally retracts the cutter proximally when the implant is released.

In some embodiments, the inflation port (feature (m) above) includes a body, a tubular passage, wherein one end of the passage is coupled to the body, and the other end terminates in a fitting connectable to a source of inflation fluid; end sections on proximal and distal ends of the body including portions formed of a resilient material, wherein the distal end section is coupled to the dilation unit inflation tube and provides a fluid-tight rotatable seal for the dilation unit inflation tube.

In some embodiments of the invention, there is provided a mechanism for closing the implant-receiving cut by application of an adhesive, or by a clamp, or by a suture.

An aspect if some embodiments of the invention pertain to a method treating a constricted bodily lumen such as a urethra constricted due to BPH.

Optionally, in some embodiments, the method involves identifying one or more areas of the lumen requiring treatment during a planning stage, delivering an implant in a compressed condition for deployment at the treatment area, expanding the lumen in the treatment area, forming a cut in the inner surface of the tissue surrounding the constricted area; and inserting an implant into the cut to maintain the expansion of the lumen.

Optionally, delivery of the implant, expanding the lumen, forming the cut, and inserting the implant into the cut are performed using an execution device inserted into the lumen after an area requiring treatment has been identified, and wherein expanding the lumen is performed using a dilation unit comprised in the execution device, and identifying areas to be treated is performed using a planning device including a positioning unit inserted in the lumen.

Optionally, forming the cut includes rotating a cutter blade around the inner surface of the tissue defining the lumen.

Optionally, forming the cut includes connecting a cutter blade the execution device to a source of electrical or electromechanical energy. Optionally the source of electrical or electromechanical energy is a diathermy machine or a piezoelectric transducer.

Optionally, according to some embodiments, the implant is removed after a predetermined time. Alternatively, the implant is formed of a material that is biodegradable.

Optionally, the implant is an open generally C-shaped ring.

Optionally, in embodiments, for which the method is applied to treatment of BPH, the implant is released for deployment with its open side facing the rectum wall.

In some embodiments, the planning device is comprised of an expandable anchoring element and a delivery element for the anchoring element, and the method includes anchoring the planning device at a desired location in the lumen using the anchoring element. Optionally, desired deployment locations are identified visually during the planning stage relative to a first set of position reference markers comprised in the positioning unit, using an optical device inserted into the lumen and the identified deployment locations are identified during the execution stage relative to a second set of position reference markers visible outside the lumen and positionally correlated with the first set of position reference markers.

According to some embodiments, the dilation unit is comprised of a balloon and a delivery tube for the balloon, and the constriction is expanded by inflating the dilation balloon through its delivery tube. In some embodiments, the anchoring element is a balloon, and the anchoring and dilation balloons are inflated using a liquid as an inflation fluid.

According to some embodiments, the positioning unit remains in the lumen after completion of the planning stage and is coupled to the execution device for use during the execution stage.

An aspect of the invention pertains to deployment of multiple implants. In some embodiments, this is accomplished by delivering two or more implants to the area to be treated at one time, forming cuts for all of the implants at the same time, and releasing all of the implants for deployment simultaneously. Optionally, the implants are delivered one at a time, using a single unit for delivery of all the implants or a separate device for each implant, and cuts for the implants are formed at the time the respective implants are delivered.

According to some embodiments, the tension applied during the execution stage is selected in reference to visible markers on an operating handle for the execution stage device or according to an audible or visual signal provided by a pressure indicator according to tension applied during the planning stage.

In some embodiments, the execution stage device is attached to a holder on a surgical table to maintain tension applied during the execution stage.

In some embodiments, the cut is optionally formed by a cutter delivered to the implantation site, or by the implant, or by cooperation of a cutter and the implant.

In some embodiments, the method includes closing the implant-receiving cut after deployment of the implant by application of an adhesive, or by a clamp, or by a suture.

Treatment Environment

FIG. 1A illustrates schematically a male bladder 100, a portion of the urethra 102, and a normal prostate 104 surrounding the urethra downstream of the bladder.

Figure 1B:
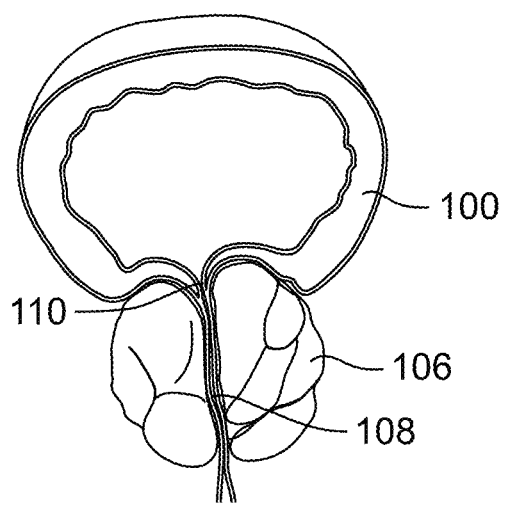
FIG. 1B illustrates constriction of the urethra due to an enlarged prostate.

In contrast, FIG. 1B illustrates the effect of enlargement of the prostate due to BPH (Benign Prostatic Hyperplasia). As may be seen, the enlargement of prostate 106 constricts the portion of urethra 108 passing through it as well as the neck 110 of bladder 100, resulting in the various problems discussed above. The embodiments to be described below are concerned with apparatus and methods for dilation of the constricted region, and deployment of an implant within the enlarged part of the prostate to help maintain the dilation.

As will be appreciated, constrictions of other bodily lumens are similarly treated.

Figure 2:
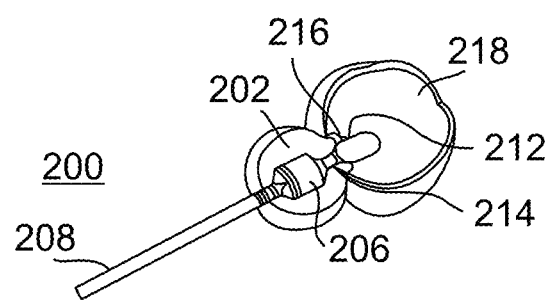
FIG. 2 is a conceptual illustration of apparatus for treating BPH according to some embodiments of the invention.

Conceptual Illustration of Apparatus for Treating BPH:

FIG. 2 shows conceptually a portion 200 of a system for treating a constructed lumen according to some embodiments of the invention. Using treatment of BPH as an exemplary embodiment, the illustrated portion of system 200 is deployed in a urethra defined by an inner surface 202 of an enlarged prostate 204. System 200 includes a dilation unit comprised of an expandable dilation element 206 carried at the distal end of a delivery element 208. Dilation element 206 is expandable to dilate the constricted urethra, and an implant 210. In some embodiments, dilation element 206 is a balloon and delivery element 208 is tube by which balloon is delivered and through which it is inflated.

In the illustrated construction, an implant 210 is carried on dilation element 206 for insertion in a cut formed on inner surface 202 of prostate 204 to help maintain the patency of the dilated urethra.

For simplicity of illustration and discussion at this stage, dilation unit 206 is shown as a single balloon. However, as explained below, in some embodiments, the dilation unit may be comprised of multiple small balloons positioned around delivery tube 208. Other forms of dilation elements, for example, resilient structures that are self-expanding, are also possible.

Distally of dilation unit 206, there is an anchoring element 212, for example, a balloon, carried on a delivery tube 214 received in dilation unit delivery tube 208. Delivery tube 214 also serves as a fluid path for inflation of balloon 212.

In use, anchoring balloon 212 is positioned in the neck 216 of bladder 218 and tension is applied to delivery tube 214 at its proximal end to retain balloon 212 firmly in place. As described below, markers (not shown) on delivery tube 214 provide a reference to help locate an area or areas at which one or more implants 210 will be deployed.

Generally stated, implant 210 is inserted in a cut, for example, a slot or groove formed in prostate surface 202. For this purpose, a cutter device (not shown for simplicity of illustration) is also delivered with dilation unit 206 and implant 210. To facilitate deployment, a working channel (not shown) may be provided by a standard cystoscope or resectoscope through which system 200 is inserted.

It should be understood that FIG. 2 is only intended as a generalized conceptual illustration and that exemplary embodiments will be illustrated and described in detail below. It should also be understood that dilation element 206 and anchoring element 212 are shown inflated in FIG. 2, but that they are delivered to the treatment site un-inflated.

Exemplary Planning Stage Device:

As mentioned above, a basic concept according to some embodiments of the invention involves separation of the implant procedure into two stages: a planning stage during which one or more areas constricted by the enlargement of the tissue surrounding the lumen are identified, and an execution stage during which the lumen is dilated and one or more implants are delivered and installed in the tissue surrounding the lumen to help maintain the dilation. In some embodiments according to this concept, each stage is performed using separate implementation devices. Preferably, however, a positioning catheter that is part of the planning device is also used during the execution stage.

Optionally, an operating handle that is part of the planning device, may also be used for both stages, as described below.

Optionally, entirely separate devices are used for each stage. Alternatively, a single operating handle can be used for both stages. As a further option, the planning and execution stages can be combined in a single unit.

Construction of Exemplary Embodiments

Planning Stage Device

Figure 3A:
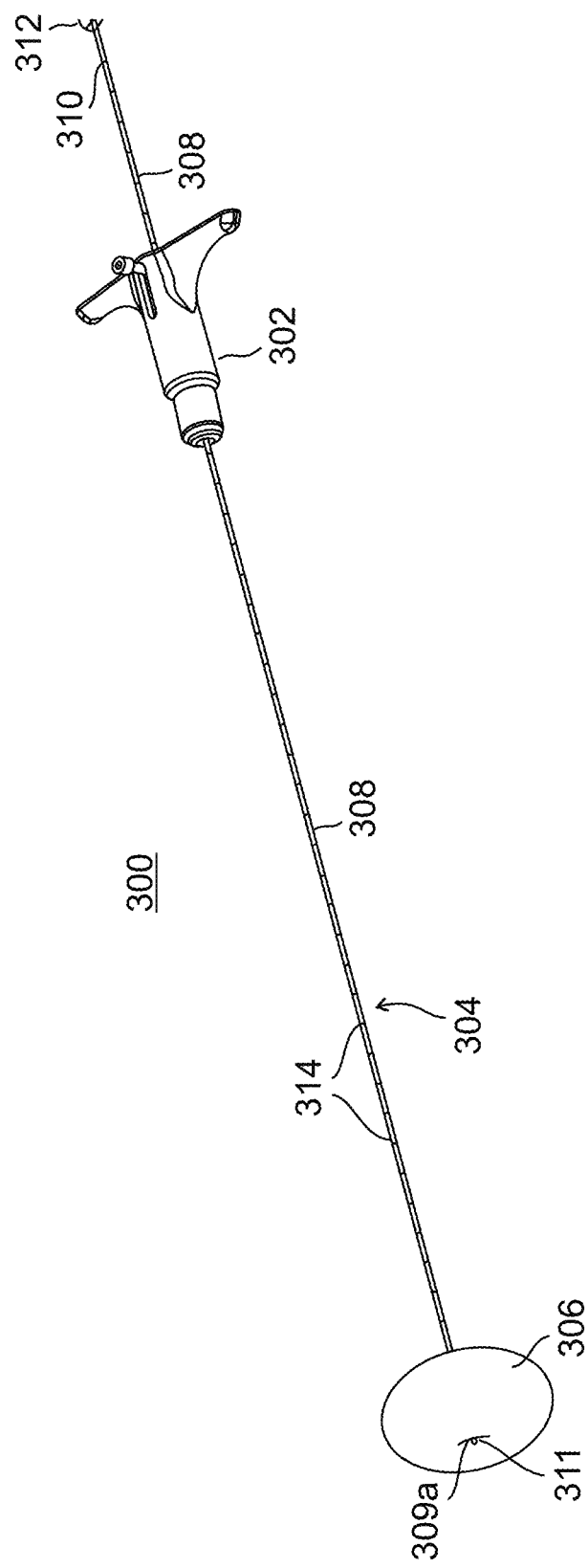
FIG. 3A is a pictorial perspective view of a device for implementing the planning stage according to some embodiments of the invention.

FIGS. 3A-3G illustrate various features of an exemplary device 300 for implementing the planning stage according to some embodiments of the two-stage concept. FIG. 3A is a perspective view of device 300 as a whole. The device is comprised of a planning catheter 304, and an operating handle 302 for planning catheter 304, Planning catheter 304 is comprised of an expandable anchoring element 306 that helps position the planning catheter at a desired location in the lumen, and a delivery element 308 formed of stainless steel, or a rigid biocompatible polymer that carries anchoring element 306 at its distal end.

In some embodiments, anchoring element 306 is a balloon that is expanded by inflation fluid provided through an interior passage in a tube forming delivery element 308. In some embodiments related to treatment of BPH, balloon 306 is shaped and sized so it fits firmly inside bladder neck 110 after it is inflated and when delivery tube 308 is pulled proximally as described below.

Figure 3C:
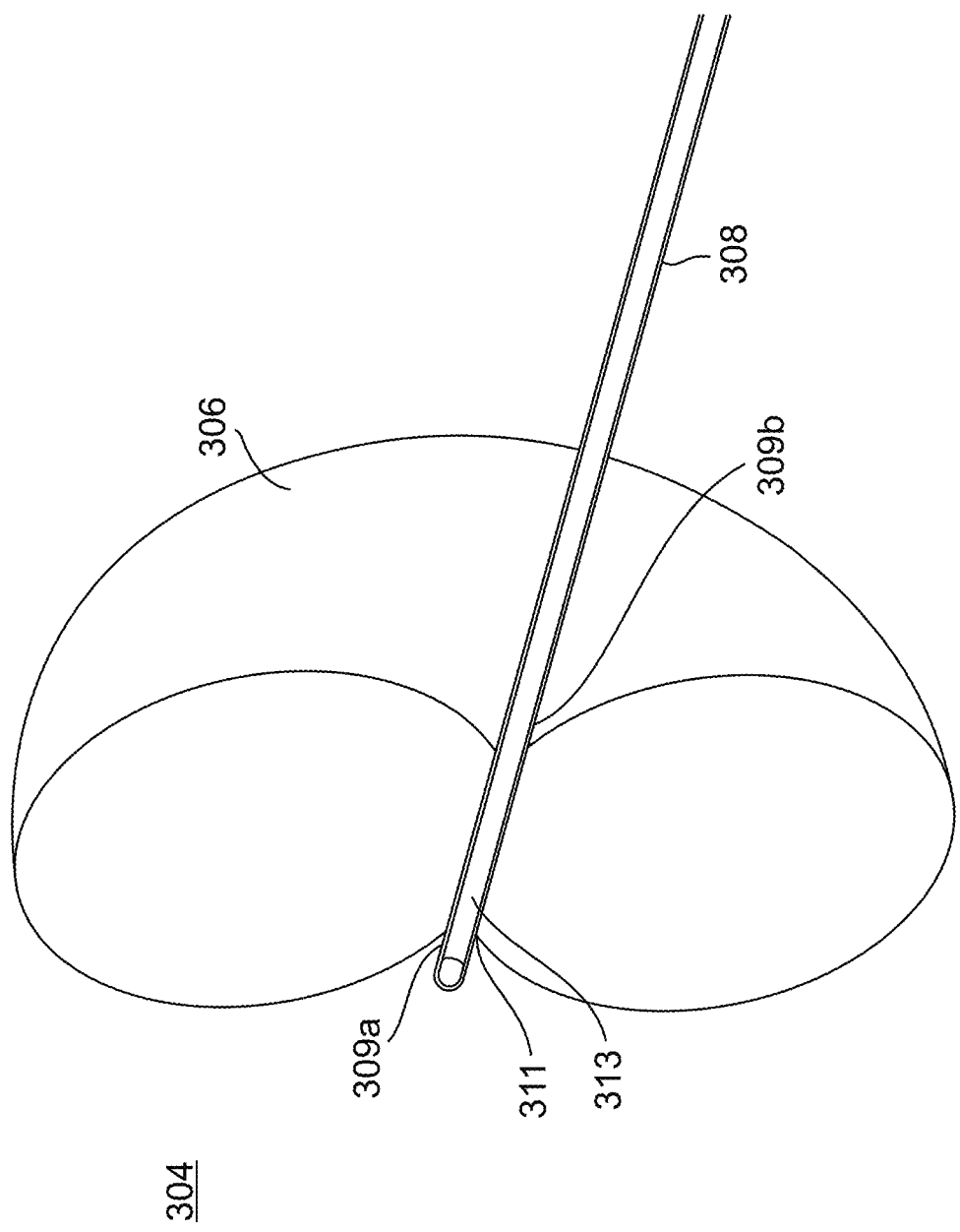
FIG. 3C is a sectional perspective view of FIG. 3B according to some embodiments.

FIGS. 3B and 3C illustrate the construction of one desirable embodiment of balloon 306 in perspective and sectional views. Notably, balloon 306, when inflated, is toroidally shaped with delivery tube 308 passing through the balloon and attached to it by a suitable adhesive at points 309a and 309b. Balloon 306 may be fabricated with the desired inflated shape, or can be spherical, and formed to the required shape by locating adhesive points 309a and 309b sufficiently close together.

Delivery tube 308 is sealed at its distal end 311, and is provided with an opening or perforations 313 inside the balloon through which the balloon is inflated and deflated.

The toroidal shape illustrated is advantageous, as compared to a spherical or other convex shape at the bladder neck in that it allows a dilation unit comprised in the execution stage device described below to be positioned closer to the bladder neck if implantation is indicated at that location.

As shown in FIG. 3A, the proximal end 310 of delivery tube 308 extends out through the proximal end of planning catheter operating handle 302 and terminates in a fitting 312 that serves as an inlet for inflation fluid provided, for example, by a hand operated syringe, a source of compressed air or a motorized or manually operated air or liquid pump.

The inflation fluid can be air, water, a saline solution or other inert liquid or gas. In some instances, it may be preferable not to use air or other gas in case of malfunction causing the balloon to expand excessively or burst due to over-pressurization or any other damage.

Advantageously, fitting 312 includes a check valve so that the source of inflation fluid can be disconnected without anchoring balloon 306 becoming deflated. As will be understood, balloon 306 is deflated by opening or removing the fitting 312 from the end of inflation tube 308 and, in the case of a liquid inflation fluid, by application of suction if necessary. As will further be understood, the outer diameter of check valve fitting 312 is small enough that it does not interfere with removal of handle 302 at the end of the planning stage, or insertion of delivery tube 308 into the execution stage device as described below.

Alternatively, instead of a balloon, anchoring element 306 may be a resilient expandable element delivered in a compressed configuration on a suitable rod or wire within a covering sheath. For example, anchoring element 306 may be an expandable cone, or a set of resilient fingers as described in PCT Application IL 2012/050094 published as WO 2012/123950, the content of which is incorporated herein by reference as if fully set forth. Such an anchoring element can be expanded by retraction of its covering sheath or by being pushed out of its sheath on its delivery rod and may be contracted for withdrawal by pulling the delivery rod back into the sheath.

In the illustrated exemplary embodiment, delivery tube 308 is releasably coupled to planning catheter operating handle 302 as described in connection with FIGS. 3D-3G below. Consequently, delivery tube 308 and anchoring balloon 306 can be separated from handle 302 and can remain in the lumen, for example, in case of treatment for BPH, with the balloon remaining in the bladder neck after the planning stage has been completed. Alternatively, the execution device may include a separate positioning device. In such embodiments, the entire planning stage device is removed at the end of the planning stage, and a separate anchoring element is provided by the execution stage.

Operating handle 302 is constructed with mechanical features needed only for the planning stage. Alternatively, as previously mentioned, a single operating handle can be provided to control the functions of both the planning stage device and the execution stage device. Separate dedicated operating handles may be advantageous in that a dedicated operating handle for the planning stage device will be of simpler construction and therefore less costly, and more convenient for the surgeon to use.

Figure 3D:
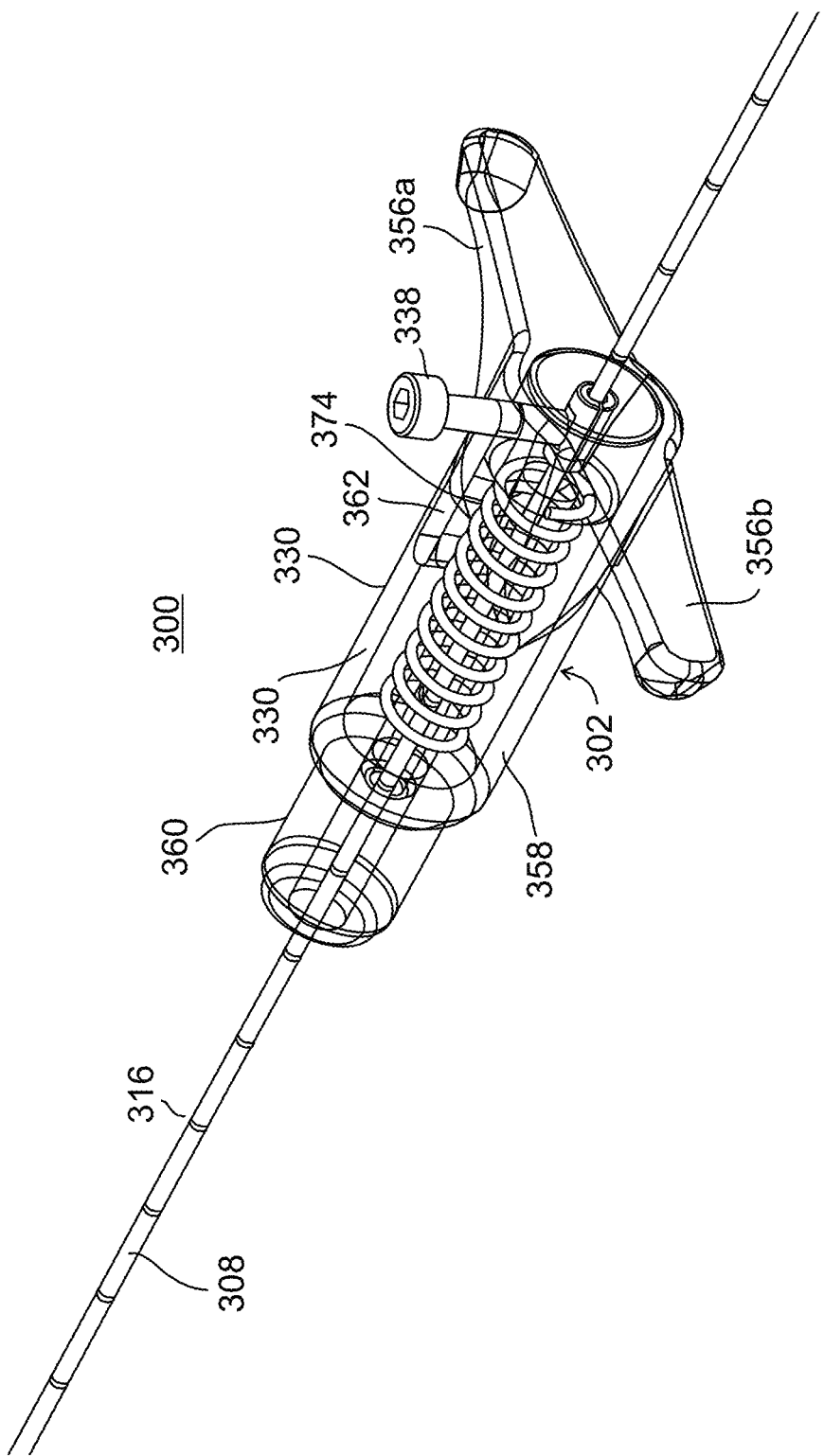
FIG. 3D is a perspective view seen generally for one side and from above, of the handle body shown in FIG. 3A emphasizing features relevant to a tensioning mechanism for the anchoring element according to some embodiments.
Figure 3E:
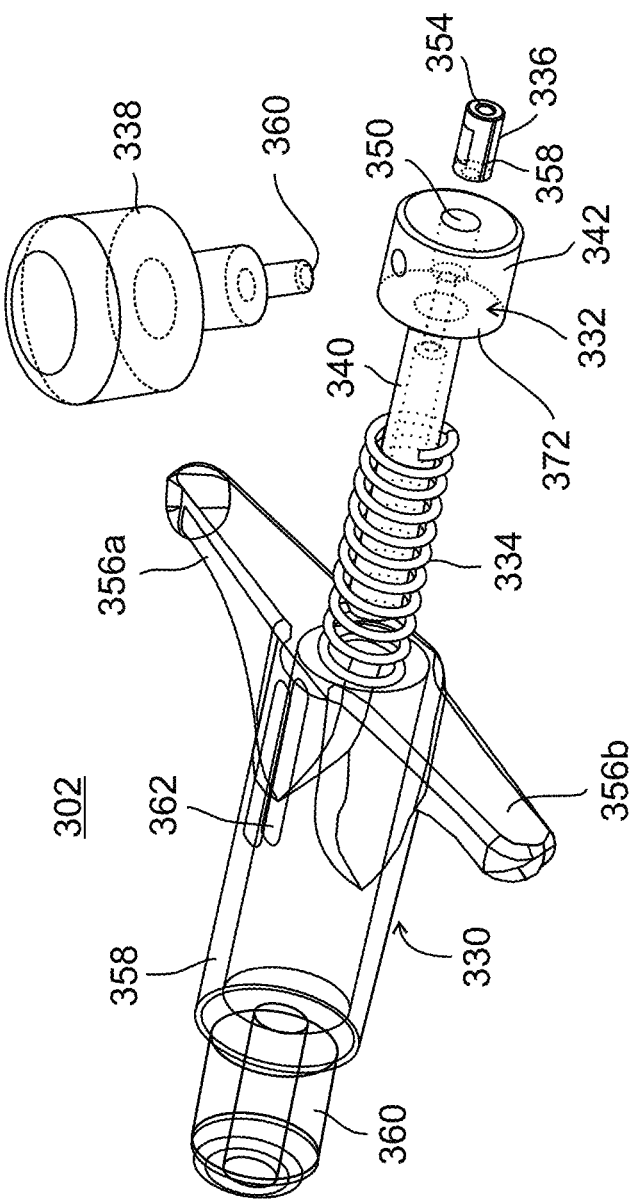
FIG. 3E is an exploded view of FIG. 3D.
Figure 3F:
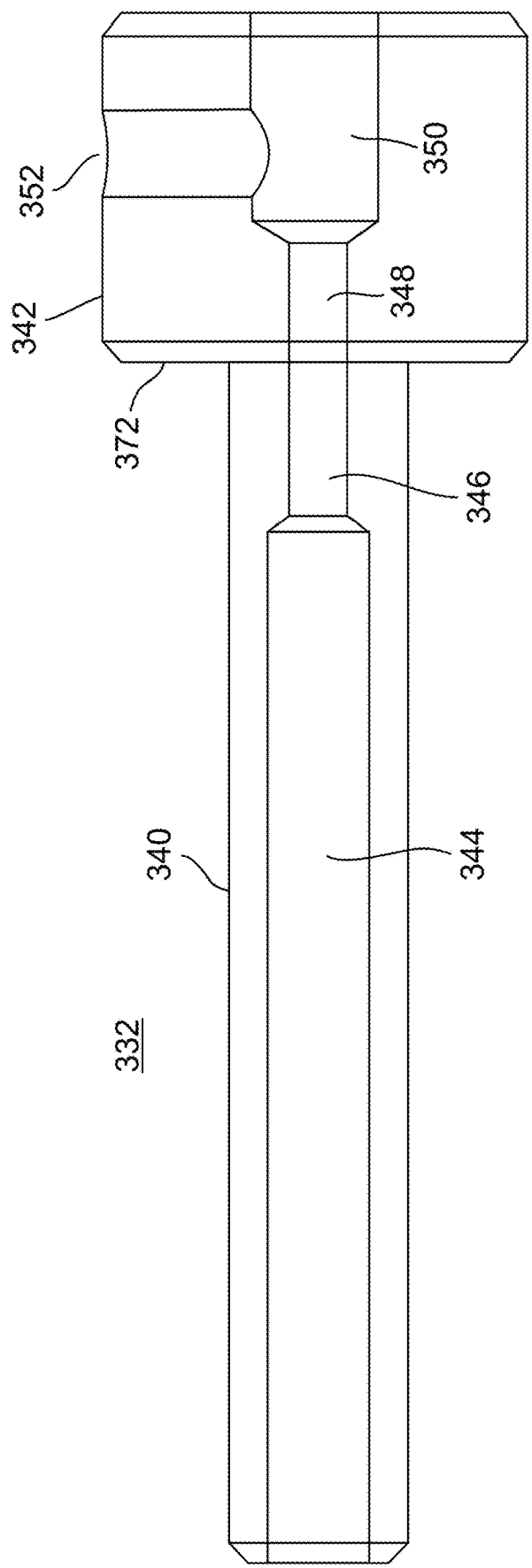
FIG. 3F is an enlarged side view of a handle guide which is part of the tensioning mechanism of FIG. 3D according to some embodiments.
Figure 3G:
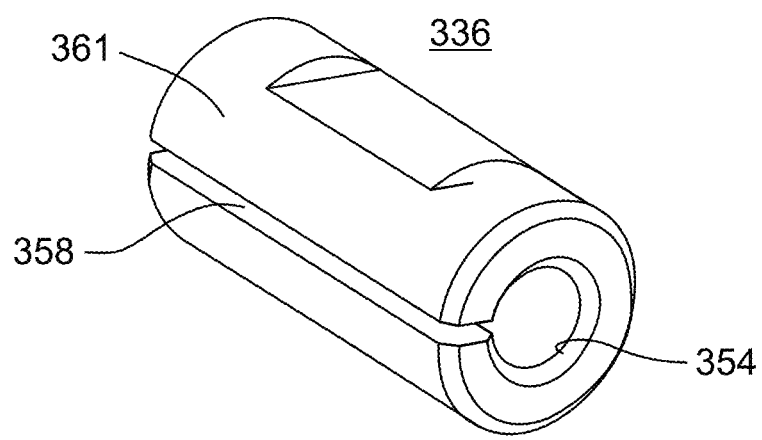
FIG. 3G is a perspective end view of a tube lock cylinder which is part of the tensioning mechanism according to some embodiments.
Figure 3H:
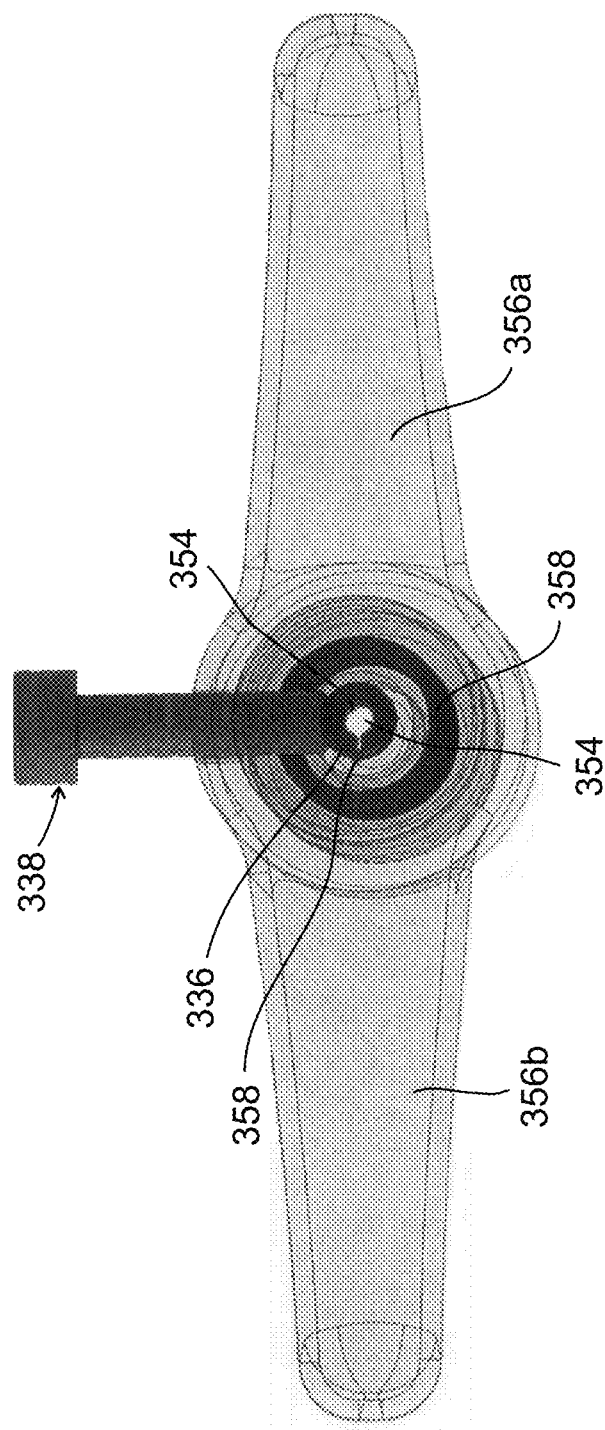
FIG. 3H is an end elevation view of the assembled tensioning mechanism of FIGS. 3D-3G.

FIG. 3D is a perspective assembly view of the construction of an exemplary planning catheter operating handle 302 with some parts transparent to show internal details, and with planning catheter delivery tube 308 in place. Planning catheter operating handle 302 is comprised of a hand grip or pull-handle 330, a pull handle guide 332, a compression spring 334, a tube lock cylinder 336, and a locking screw 338. FIG. 3E shows these elements in an exploded view. The configuration of handle guide 332 is shown in FIG. 3F. FIG. 3G is an enlarged perspective view of tube lock cylinder 336, and FIG. 3H is a proximal end elevation of the assembly of FIG. 3D.

The functions of planning catheter operating handle 302 are to facilitate delivery of anchoring balloon 306 to its position of use, for example, in the neck of a bladder, and to apply tension through delivery tube 308 to lodge balloon 306 firmly in the bladder neck. This permits accurate identification of required implantation sites in conjunction with the optical unit of the working channel, and accurate and repeatable location of the intended implantation sites during the execution stage.

In the illustrated embodiment, pull handle 330 is comprised of gripping wings 356a and 356b, a tubular proximal barrel portion 358 and a tubular distal barrel portion 360. Proximal barrel portion 358 includes a longitudinal slot 362 which permits the handle to slide along locking screw 338 when the handle is pulled proximally to apply tension as described below.

As shown in FIGS. 3E and 3F, handle guide 332 is a generally tubular structure comprised of a cylindrical body portion 340 and a cylindrical head portion 342 having an outside diameter larger than that of body portion 342. The interior of body portion 340 is defined by first inner passage 344 and a smaller internal diameter second inner passage 346, which serves to center delivery tube 308 and tube lock cylinder 336.

The interior of head portion 342 includes a first axial passage 348 which is a continuation of passage 346 and a larger-diameter second axial passage 350. Passage 350 is sized to receive tube lock cylinder 336 (see FIGS. 3D and 3G). Head portion 342 also includes a threaded radial passage 352 that receives tube locking screw 338.

Still referring to FIGS. 3D through 3H, planning catheter operating handle 302 is assembled with spring 334 mounted on body portion 340 of handle guide 332, and these are positioned within the proximal body portion 358 of pull handle 330. Tube lock cylinder 336 is positioned within axial passage 350 in handle guide head portion 342 (see FIGS. 3E and 3G). The tensioning mechanism as a whole is mounted in any suitable manner within pull handle barrel portion 358.

Referring still to FIGS. 3E and 3G, tube lock cylinder 336 includes an interior passage 354 and a longitudinal gap formed by a through-slot 358. Anchoring element delivery tube 308 is sized to slide freely through the interior of tubular portions 344 and 346 of pull handle guide 332 and through interior passage 354 in tube lock cylinder 336. When locking screw 338 is tightened, its end 360 presses on a flattened portion 361 of tube lock cylinder 336 causing gap 358 to close. This allows cylinder 336 to grip delivery tube 308, locking the tube in place relative to the handle assembly. It will be understood that cylinder 336 is formed of a resilient material, for example, stainless steel, so that it returns to its relaxed position when screw 338 is withdrawn, allowing delivery tube 308 again to slide freely. Use of the slotted tube lock cylinder may be advantageous as it minimizes the risk that tube 308 will be damaged when screw 338 is tightened.

Thus, when handle 330 is pulled proximally, slot 362 slides along screw 338 and spring 334 is compressed by pull handle barrel portion end surface 370. Consequently, spring 334 applies pressure against handle guide head end surface 372. With delivery tube 308 locked in handle guide 340 by screw 338, the delivery tube is pulled proximally, causing anchoring balloon 308 to lodge firmly against the inside of the bladder neck.

As will be understood, the more handle 330 is pulled proximally, the greater will be the tensioning force applied to balloon 308. It will also be understood, that the tension applied to balloon 308 should be the same in both the planning and execution stages to permit repeatable location of positioning catheter 304 during both stages. To facilitate this, as shown in FIG. 3D, tensioning markers 374 are provided along the longitudinal edges of slot 362 and on the execution stage operating handle as described below.

As noted above, positioning catheter 304 provides a positional reference element relative to which the deployment locations for one or more implants are determined during the planning stage. For this purpose, as illustrated in FIG. 3A, delivery tube 308 includes a series of circumferential markers, two of which are indicated at 314, spaced at intervals along the tube near its distal end proximally of balloon 306. These are visible using the optical device associated with the working channel and allow the surgeon to reproducibly determine the implant deployment locations relative to the bladder neck when tension is applied to delivery tube 308. The spacing between the markers may be in the range of about 1 mm to about 10 mm for example, about 5 mm.

By way of example, in the case of the anchoring element being a balloon, and for treatment of BPH, during the planning stage, pull handle 330 is locked at a convenient position along balloon delivery tube 308 by tightening screw 338, and anchoring balloon 306 is positioned in the bladder and inflated. Then, using the optical device for guidance, a suitable level of tension is applied by pull handle 330 to lodge balloon 306 firmly against in the bladder neck.

Still using the optical unit, the surgeon notes the position closest to the bladder neck at which an implant should be deployed, as well as the other positions, if any, at which deployment of implants would be desirable.

After the surgeon has determined the implant deployment locations, the planning stage is complete. The optical unit is then withdrawn to allow insertion of the execution stage device. As will be understood, with the optical unit removed, distal markers 314 can no longer be used to locate the intended implantation sites. In some embodiments, a set of markers 316 located at the proximal end of tube 308 are used for this purpose as described below.

In those embodiments in which planning catheter 306 is reused in the execution stage, planning catheter operating handle 302 is disconnected from the planning catheter, for example, by loosening screw 338 and sliding the handle in the proximal direction. Accordingly, when the execution stage device is inserted in the working channel, it is positioned so that the proximal end of the execution stage planning catheter is received within it so that it can be used during the execution stage as described below.

External Features of an Exemplary Execution Stage Device

Figure 4A:
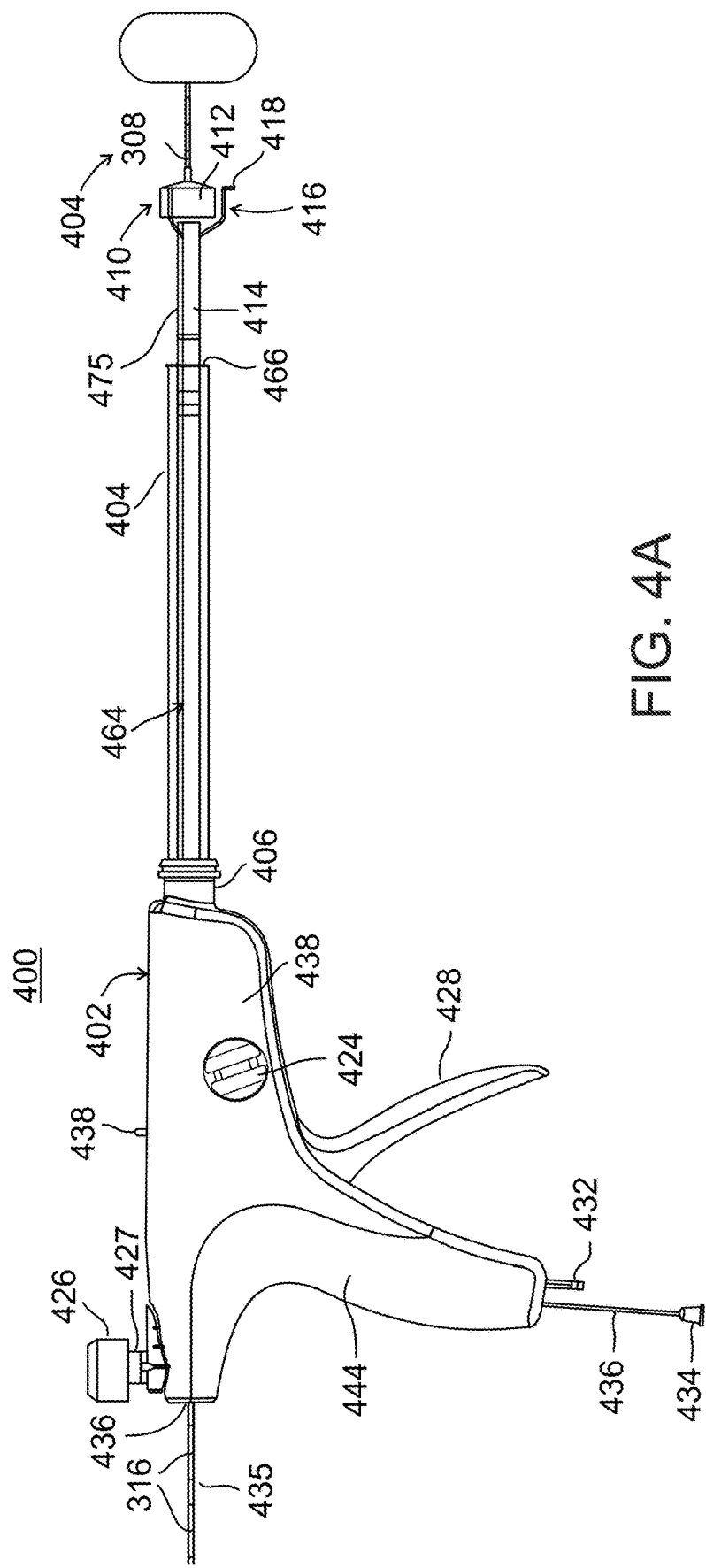
FIG. 4A is side elevation view of an execution stage device according to some embodiments.

FIG. 4A is a side elevation showing some of the operational features of an exemplary execution stage device 400 in which the operating handle is separate from the one used for the planning stage device. Execution stage device 400 includes an operating handle 402 that may, for example, be generally pistol-shaped with a barrel portion 438 and a grip portion 444. Other external structural features include a retractable outer sheath 404, a coupler or adapter 406, for example, a threaded or bayonet type, at the distal end of operating handle 402 for connection to a complementary fitting on the device serving as a working channel. The above-identified parts are formed of suitably strong and rigid metal, for example, aluminum or stainless steel, or a suitable biocompatible polymer.

The distal end 466 of outer sheath 404 is shown proximally retracted to a point 466 so that a dilation unit 410 including a dilation balloon 412, and a delivery tube 414, a cutter 416, and a delivery tube 475 for an implant release mechanism 422, that are contained within the outer sheath to the implantation site are visible. These are described in connection with FIG. 4B below.

An electrical connector 432 provides an inlet for a source of electrical or electromechanical power, for example, a conventional diathermy machine or a piezoelectric transducer, to provide electrical power to the blade of cutter 416 that forms an implant-receiving cut. Also, a fluid connector 434, for example, a standard Luer type connector, is provided for connection to a source of inflation fluid for dilation balloon 412 through a fluid conduit 436 and an inflation port described below within handle 402. Preferably, the inflation fluid for balloon 412 is a liquid for the reasons stated above.

It will be recalled that in some embodiments, the positioning catheter 304 used during the planning stage is coupled to execution device 400 for reuse during the execution stage, but that in other embodiments, execution device 400 includes a dedicated planning catheter. Both situations are represented by planning catheter 304 shown at the distal end of execution stage device 400, and with the proximal end 435 of its inflation tube 308 extending out of the proximal end of operating handle 402 at 436.

Operating handle 402 also includes actuators for the execution stage functions. These include a trigger 428 to operate a mechanism that rotates a cutter to form an implant-receiving cut on the inner surface of the tissue surrounding the constricted area of a 4A bear the same reference signs as in FIG. 4A. lumen, two knobs 424 on opposite sides of handle 403 which serve as actuators for the mechanism to retract and extend outer sheath 404, a locking screw 426 for locking the positioning catheter to the operating handle, a tension indicator 425, and a lever 438 that actuates an implant release mechanism. Two knobs 424 are provided on the opposite sides of operating handle 402 to accommodate use by the left or right hand.

It should be understood that execution stage device 400 is intended as a non-limiting example and may include different and/or other structural features and/or actuators, as well as internal components as described below.

For example, in an unillustrated variation, the operating handle for the execution stage device may be constructed without a tensioning mechanism. In such an embodiment, the planning stage operating handle which contains its own tensioning device can be attached to the proximal end of the execution stage operating handle to provide the required tensioning mechanism. Any suitable arrangement for coupling the handles together may be employed.

Parts that perform the actual execution stage functions inside the lumen are shown enlarged in FIG. 4B, again for example, in an embodiment in which the planning catheter 304 of planning stage device 300 is reused in the execution stage device. These parts include a dilation unit 410 comprised, for example, of a balloon or other expandable element 412 mounted on a delivery tube 414, a rotatable cutter 416 comprised, for example, of a blade 418 and a pusher wire 462 carried for delivery within a tube or inner sheath 420, and an implant carrier and release mechanism 422 comprised for example, of a release pin 468 and a carrier tube 475.

Briefly, dilation unit 410 is expanded to enlarge the lumen before or during deployment of one or more implants. Cutter 416 forms a cut on the inner surface of the tissue surrounding the lumen (for example, the inner surface of the prostate that defines the urethral passage through the prostate).

Dilation element delivery tube 414 is comprised of an outer tube 414a and a concentric inner tube 414b. The two tubes 414a and 414b are formed for example, of stainless steel and are partially welded together near their respective distal ends to form a rigid assembly while also providing an annular passage 414c between the tubes for inflation of balloon 412. Optionally, the tubes may be partially welded at their respective proximal ends as well. Outer section 414a terminates within balloon 412 while inner section 414b extends distally beyond the balloon.

The proximal end of balloon 412 is attached to the outer delivery tube section 414a and the distal end of the balloon is connected to inner delivery tube section 414 in any suitable manner used conventionally for assembly of devices such as balloon catheters. 412. Consequently, the opening at the distal end of outer tube 414a serves as an inflation port for balloon 412.

Also, as may be seen in FIG. 4B, anchoring balloon delivery tube 308 extends through and distally beyond inner tube section 414b, and therefore a separate fluid-tight seal around tube 308 is not required. In those embodiments for which planning catheter 304 is reused during the execution stage, tube 308 is inserted into tube 414 so that it extends out through the proximal end of operating handle 402 (see FIG. 4A).

In some embodiments, cutter 416 is used to form one or more implant-receiving cuts in the tissue surrounding the lumen. In some embodiments, implant carrier and release mechanism 422 delivers an implant to the deployment site and includes an element 468, for example, a pin or a rod, operable from the control handle to release the implant for deployment in the cut formed by blade 418. For convenience, implant carrier and release mechanism 422 will sometimes be referred to herein simply as the "implant carrier".

Dilation unit 410, cutter 416, implant carrier 422, and an implant pusher assembly (the latter described below in connection with FIGS. 5N and 5O), are contained within outer sheath 404 during delivery of execution device 400 through the working channel to the treatment site and are exposed when outer sheath 404 is retracted to the position shown at 466 in FIG. 4B, for example, about 10 cm. In this connection, it will be understood that dilation balloon 412 which is delivered un-inflated within sheath 404, has been shown inflated in FIG. 4B. Similarly, cutter blade 418 which is delivered, inside sheath 420 according to some embodiments, is shown pushed out of the sheath and with blade 418 in its operative position extending outwardly toward the tissue surrounding the lumen, as described below.

The components shown in FIG. 4B are formed of suitable biocompatible materials. Balloon delivery tube 414 is formed of a rigid material, for example, stainless steel. Balloon 412 may be formed of nylon or PET. Cutter blade 418 is formed of a resilient metal, for example, nitinol, or stainless steel. Cutter delivery tube 420 and implant carrier 422 may be formed of a suitable polymer, for example, PEEK, polyethylene, Pebax®, or Nylon®. The parts identified above and their respective actuator mechanisms are described in more detail below.

Referring still to FIG. 4B, in some embodiments, cutter sheath 420, and implant carrier 422 are attached to dilation balloon outer delivery tube section 414a, for example, by adhesive or spaced collars up to a few centimeters, for example 3-5 cm, from the proximal end of balloon 414. This allows cutter pusher wire 462 and delivery tube 420 to bend to remain in contact with the balloon as it is expanded.

In other (unillustrated) embodiments, cutter delivery tube 420 and implant carrier 422 are not attached to balloon delivery tube 414, but are delivered as separate units within outer sheath 404. Optionally, the cutter sheath and the implant carrier may be attached together for delivery.

As will be appreciated, in any of the above-described embodiments, blade 418 is be rotated to form the cut around the lumen. In those embodiments in which cutter delivery tube 420 and implant carrier 422 are attached to balloon inflation tube 414, the tube itself is rotatable and in turn, rotates the cutter and the implant carrier. If cutter 416 and implant carrier 422 are not mounted on dilation balloon inflation tube 408, only cutter tube 420 and implant carrier 422 are rotated.

Rotation may be provided by a suitable mechanism such as described below within operating handle 402 actuated by trigger 428 (see FIG. 4A). Alternatively, the rotation mechanism may be actuated manually by a knob. As another alternative, a motor may be provided in handle 402 to provide the rotation.

In some embodiments, when balloon 412 is inflated as shown in FIG. 4B, it bears on cutter sheath 420 to press the end 458 of blade 418 against the tissue to be cut, thereby to assist in formation of the cut. In embodiments in which the cutter is rotated by inflation tube 414, balloon 412 also rotates, so cutter sheath 420 does not move relative to the balloon. This may be desirable as it may protect the balloon from possible damage due to movement of cutter sheath 420.

Figure 4D:
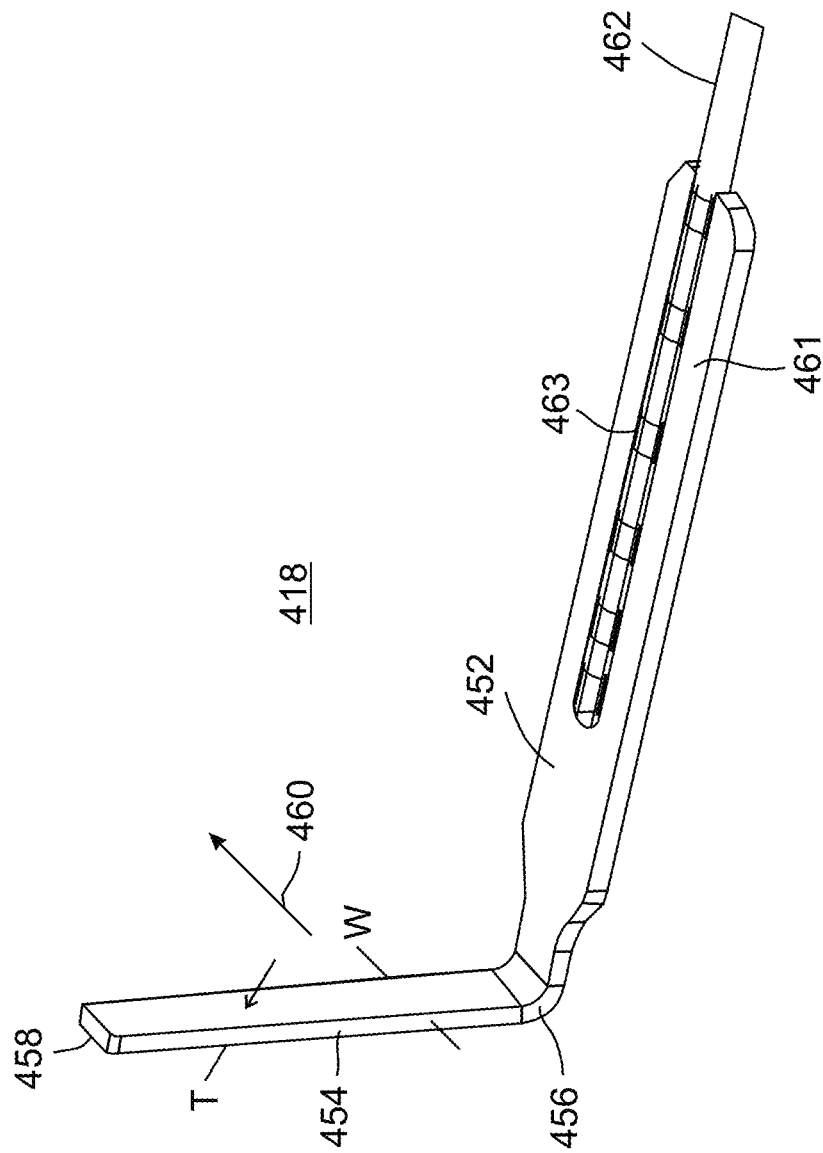
FIG. 4D is a perspective view of an exemplary cutting blade comprised in the execution stage device shown in FIGS. 4A and 4B according to some embodiments.

However, even those embodiments in which only the cutter and the implant carrier are rotated, balloon 412 may be sized so that when it is fully inflated, it bears on sheath 420 so that the edges 454 and 458 of blade 418 are pressed against the tissue to be cut to assist in making the cut (see FIGS. 4B and 4D).

FIG. 4B and the enlarged fragmentary view of FIG. 4C also illustrate part of the implant delivery and release mechanism 422 according to some embodiments. This is comprised of implant release pin 468, the distal end 474 of which forms a projection that engages a small loop 470 attached through a hole 471 at one end of an implant 472. Loop 482 is small enough that it lies within the implant-receiving cut and does not interfere with the function of the implant.

Pin 468 extends through a tube 475 within outer sheath 404 into operating handle 402. A retraction mechanism in handle 402 is coupled to pin 468 and is operable to pull pin 468 proximately to withdraw projecting pin end 474 out of loop 470 to release the implant. Like cutter delivery tube 420, implant carrier tube 475 and releases pin 468 are sufficiently flexible that they can bend as balloon 412 is expanded.

An exemplary mechanism for retracting release pin 468 is described in connection with FIG. 5K below.

As shown in FIGS. 4B and 4C, and as described in the previously mentioned '229 International Application, implant 472 is advantageously an open ring, for example, C-shaped, formed of a suitable resilient material.

One advantage of the open-ring configuration, particularly in treatment of BPH, is that because of the lobular shape of the prostate, it is hard to achieve a full circular cut of a suitable uniform depth. For example, at the "junctions" of the lobes, deeper penetration of the blade may be needed to help assure that the implant is deployed fully within the prostate tissue, but such deeper penetration may cause perforation in other areas of the prostate, which may pose a safety issue.

Moreover, the main "junction", i.e., the area of the greatest variation in the prostate surface is located generally facing the rectum, and orienting the implant so that its opening faces in that direction (and will not require implantation) increases the probability that the implant is fully within the prostate and the probability that it will be fully covered by a new tissue growth layer without the need for a deep cut and undue risk of perforation.

Open-ring implants may also be desirable in that one size implant may be used for lumens of various internal dimensions.

After balloon 412 is fully expanded, and the implant is released from sheath 404, the implant rests on the balloon surface but is prevented from expanding to its full size because it is still held on pin 468. Advantageously, implant 472 is still at least partially compressed when it is seated in its cut. This allows the implant to exert radial force on the lumen to help prevent it from re-collapsing.

It should be appreciated that implant end 469 does not need to be restrained because the implant is delivered rolled up inside sheath 404 and it unrolls due to its resiliency when sheath 404 is retracted.

Other constructions arrangements for delivery and release of implant 472 are also possible according to some embodiments of the invention. For example, in an unillustrated variation, a small pin is mounted on the trailing end of cutter blade 418. A small hole at the leading edge of the implant receives the pin so that the cutter serves as the implant carrier. As the cutter rotates, the implant follows it into the cut due to its resiliency. A trigger wire such as that employed in the embodiment shown in FIGS. 4B and 4C separates the implant from the cutter pin when the cut has been completed. It should be appreciated that in such an embodiment, the implant itself participates in formation of the cut.

FIG. 4D shows the construction of cutter blade 418 according to some embodiments of the invention, with delivery tube 420 removed. In the illustrated embodiment, blade 418 is a unitary L-shaped element formed, as previously noted, of a resilient material such as nitinol. The blade includes a longitudinally extending proximal leg portion 452 and an erectable distal leg portion 454 separated by a flexible area 456 that functions as a hinge. As noted, blade 418 is a single part. It may be formed, for example by laser-cutting and heat-treatment to provide the flexibility to be bent at 456 under pressure and to return to its original treated structure while pressure is released. This allows distal leg portion 454 to be folded back along proximal leg portion 452 while inside sheath 420 during delivery. Due to its resiliency, when outer sheath 404 is retracted, and distal leg 454 is pushed out of sheath 420, it pops up to the position shown in FIG. 4D, approximately at a 90 degree angle.

It has been found that attention to certain features of cutter blade 418 will potentially help optimize its performance. In particular, distal leg 454, which is optionally sharpened at its outer edge 458, actually forms the cut. However, since the blade is formed of a resilient material such as nitinol, it should be dimensioned to help assure that the cut is formed cleanly and with minimum risk of tissue damage.

Taking the foregoing into account, it has been found to be potentially advantageous that the width W of distal blade portion 454 be great enough in the direction tangential to the cutting direction (indicated by arrow 460) that it is sufficiently stiff to retain its shape.

At the same time, dimension W should not be so great that, when the blade is folded, the required diameter of delivery sheath 420 and/or outer sheath 404 is so great that insertion of outer sheath 404 into the lumen, for example, through the working channel, becomes a problem.

Further, a wide blade may require higher energy while performing the cut, which can increase the risk of damage to the surrounding tissue. In summary W should be selected to retain its shape while the cut is being made and without risk to damage to surrounding tissue and without undesirable enlargement of the diameter of the outer sheath. Taking the foregoing factors into consideration, it has been found that good results may potentially be obtained if W is selected within the range of about 0.2 mm to about 3 mm, for example, about 0.9 mm.

Other considerations that have been found to be important include the following:

(a) the length of distal blade portion 454 should be selected according to the desired depth of cutting. If blade portion 454 is too long; the risk of perforation of the tissue in the cutting area may be increased. On the other hand, if blade portion 454 is too short, the cut may be superficial, and the entire implant may not be seated in the cut. That may interfere with new tissue overgrowth. Taking the foregoing into account, good results can potentially be achieved if L is selected within the range of 2-20 mm for example 6 mm for treatment of a prostate;

(b) blade portion 454 should be thin to give the blade the flexibility to be folded into its delivery tube 420 or outer sheath 404 for delivery and withdrawal. In addition, a thin sharpened edge may require lower energy which may require that cutting is also done mechanically (as with a knife). On the other hand, if is too thin, the blade could be deformed due to thermal effect caused by electrical current during cutting. Taking the foregoing into account, good results can potentially be obtained with a blade thickness T in the range of 0.15-0.3 mm for example 0.22 mm.

Still referring to FIG. 4D, proximal leg 452 of blade 418 is attached to a pusher wire 462 for example, at several weld points 463 between the legs of a fork-shaped end portion 461. Pusher wire 462 extends through inner sheath 420 and outer sheath 404 into operating handle 402 from which it is manipulated by the surgeon to push blade portion 418 out of sheath 420 for use, and to retract it back into the sheath for removal. It will be appreciated that when blade 418 is retracted, distal leg 454 bends in the opposite direction from its delivery position so that it is unfolded and extends linearly within tube 420.

Blade pusher wire 462 is connected to wire 432, which in turn, is configured for connection to a source of power for the cutter blade, as described below.

In the illustrated embodiment, there is no need to re-extend outer sheath 404 for removal of the components of implantation device 400 since cutter blade 418 is withdrawn into sheath 420 (bent in the opposite direction from its delivery orientation) and anchoring balloon 306 and dilation balloon 412, when deflated, have smaller diameters than the internal diameter of the outer sheath.

Other constructions for delivery of cutter mechanism are possible, according to some embodiments as will be understood by those skilled in the art in light of the present disclosure. For example, in an unillustrated variation of the arrangement for delivery of cutter mechanism 416 described above, blade 418 and wire 462 are delivered to the implantation site folded as previously described, without a delivery tube 420, i.e. only in outer sheath 404. When outer sheath 404 is retracted, wire 452 holds it in place longitudinally so that cutter blade 418 pops up to its operative position for withdrawal of the execution device, wire 452 is pulled proximally and the cutter is retracted into the outer sheath as previously described.

As in the case of the illustrated embodiment, there is no need to re-extend outer sheath 404 for removal of the components of execution device 400. However, it may be advantageous for cutter 416 to be retracted into sheath 404 so that cutting edge 458 does not contact and damage the inside of the working channel device.

In the illustrated example, dilation element 412 is a generally cylindrical balloon having a length in the range of about 0.5 cm. to about 5 cm. for example, 1.5 cm, and an inflated diameter in the range of about 1-50 mm, for example, 20 mm.

Alternatively, in an unillustrated variation dilation unit 410 can be formed of a plurality of smaller diameter balloons of generally cylindrical shape positioned in a circumferential ring around delivery tube 414. In such embodiments, dilation elements 440 may include between 2 and 10 separate balloons, for example 6 balloons, each having an inflated diameter in the range of about 1 mm to about 25 mm, for example, 10 mm. The length of the individual balloons 440 may be the same as that of balloon 412.

In some multiple-balloon embodiments, inflation/delivery tube 408 includes a manifold 442, for example a branched tube, at its distal end to inflate the balloons. Alternatively, each balloon may have its own inflation tube.

Multiple small balloons may be advantageous in some instances since it may be possible to use off-the-shelf items. Using a plurality of small balloons may also reduce the effect of balloon malfunction—if a single balloon is damaged or has a leak, the effectiveness of the dilation will not be significantly reduced.

On the other hand, a single balloon may be easier to design, simpler to assemble, and may give a smoother expansion of the urethral tissue and therefore may improve cutting performance.

The cut for the implant is formed preferably using electrical energy provided, for example, by a conventional diathermy machine or a piezoelectric transducer through a connector wire 432 extending through grip 444, as shown in FIG. 4A.

As a further option, in some embodiments, the implant itself is connected directly to the source of electrical energy so that it forms its own cut, e.g., by rotation on the surface of a rotatable dilation balloon or simply by radial expansion when the dilation balloon is inflated. In the latter case, the implant effectively "burns" its way into the wall of the tissue surrounding the lumen, and a separate cutter unit is not needed. Optionally, the implant may include a sharp edge to facilitate formation of the cut if the implant can rotate.

Several options for the construction and configuration of cutter 416 are shown in International Published Application WO 2012/123950, the content of which is incorporated herein by reference as if fully set forth.

Internal Construction of an Exemplary Execution Device Operating Handle

Figure 5A:
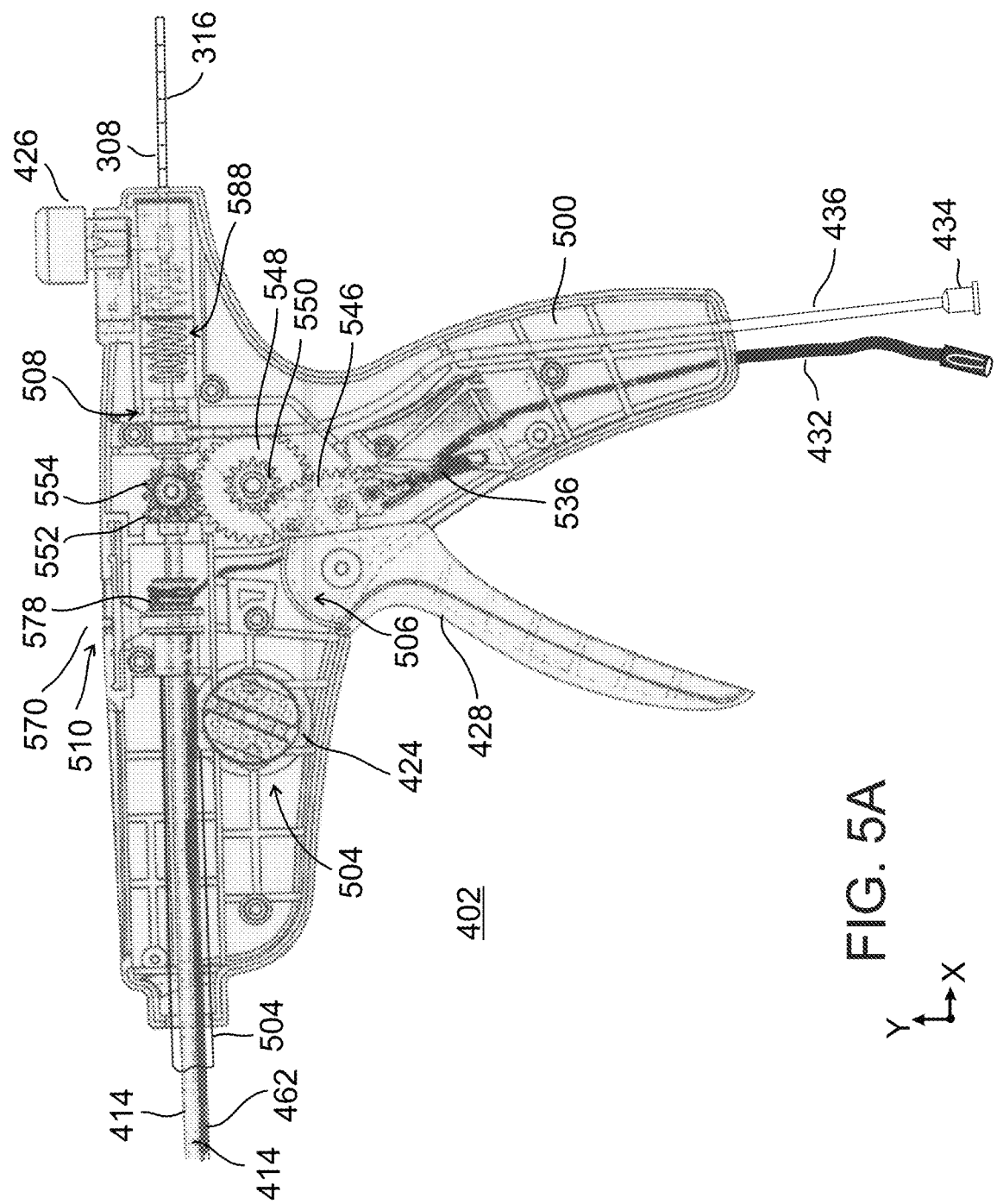
FIG. 5A is a side elevation of an exemplary operating handle for an execution stage device with a cover of the handle removed showing the internal parts according to some embodiments.
Figure 5B:
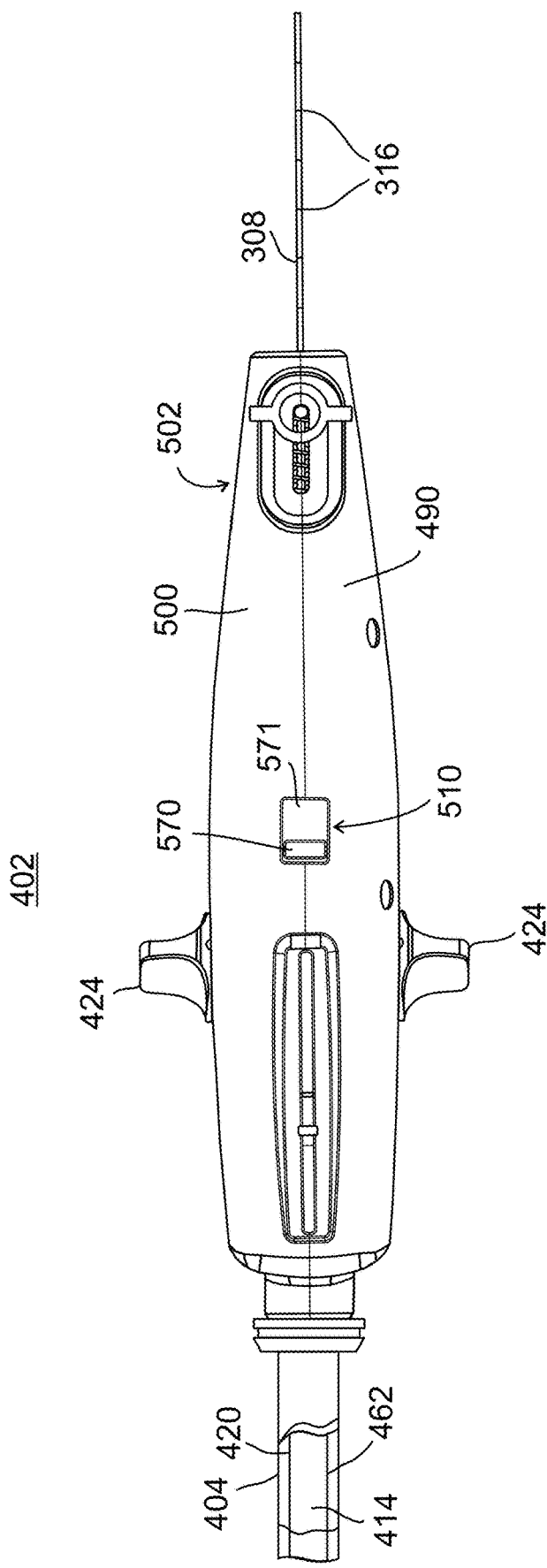
FIG. 5B is a top view of the operating handle shown in FIG. 5A.

FIG. 5A is a side elevation showing some of the operating features of an exemplary embodiment of operating handle 402, and with some parts transparent to show internal details. In the illustrated embodiment, handle 402 is formed of a body 500 on which the internal components are mounted and a side cover 490. FIG. 4A shows side cover 490 in place, while FIG. 5A shows the side cover removed to reveal the internal construction. FIG. 5B is a top view of operating handle 402 with locking knob 426 removed. For clarity, the components shown in FIGS. 5A-5C previously discussed have been omitted.

Parts located within operating handle 402 include a tensioning mechanism 502 for positioning catheter delivery tube 308, an external sheath retraction mechanism 504, a cutter rotation mechanism 506 including a connection of blade pusher wire 462 to power connector wire 432 as previously described in connection with FIGS. 4A and 4D, a dilation balloon inflation port 508, an implant release mechanism actuator 510. Handle 402 also includes an implant pusher mechanism 520 shown in FIGS. 5N and 5O. The components shown in FIGS. 5A and 5C are mounted in any suitable and desired manner in body 500, as will be apparent to those skilled in the machine design arts in light of the disclosure herein.

FIGS. 5A and 5B also show previously described external parts of operating handle 402 including external sheath 404, sheath retraction actuator knobs 424, locking knob 426 for positioning catheter delivery tube 308, cutter rotation trigger 428, cutter electrical connector 432, dilation balloon inflation tube 436, and implant release mechanism handle 438.

Figure 5C:
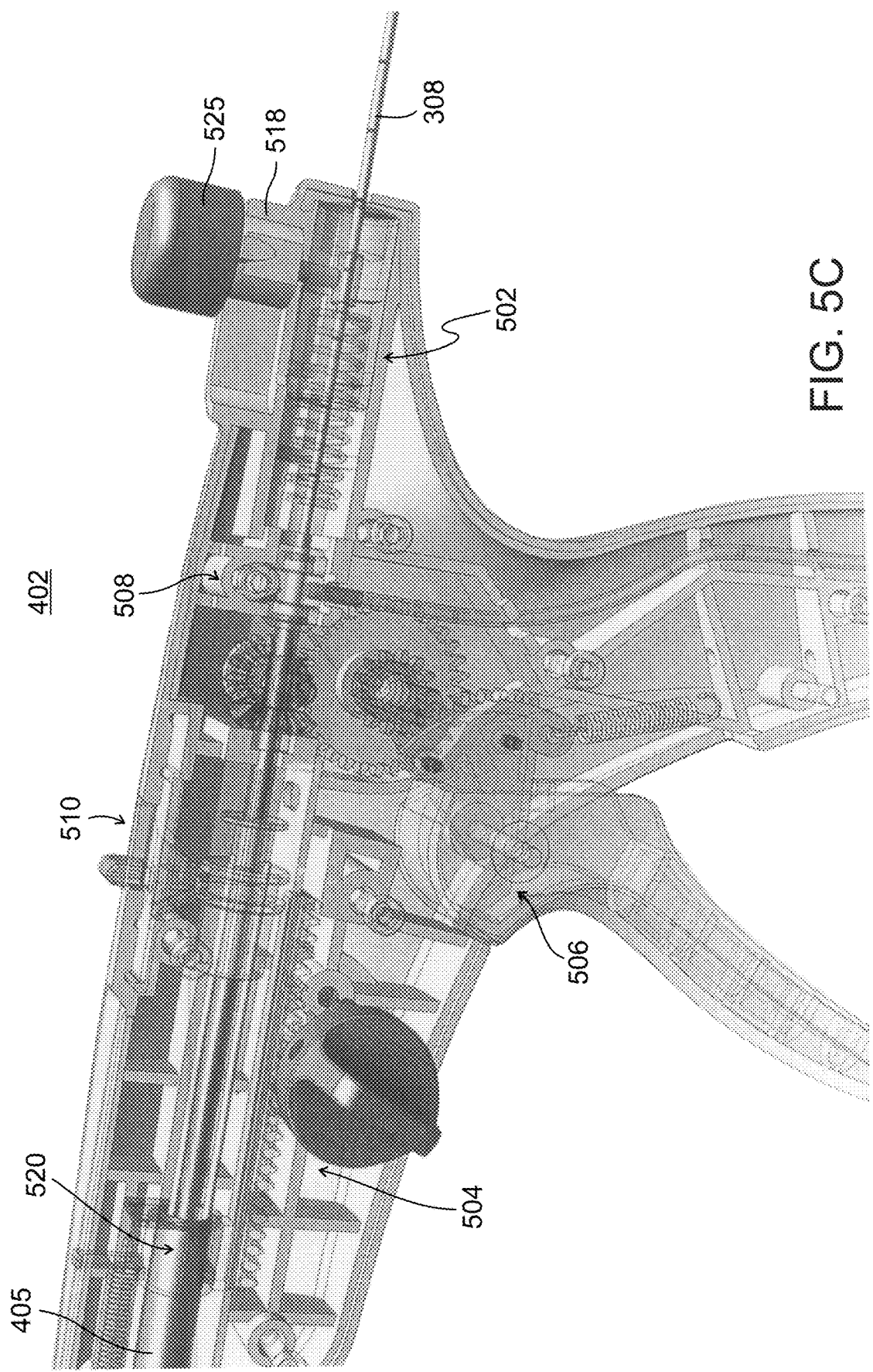
FIG. 5C is an enlarged view of part of FIG. 5A showing details of the construction of exemplary operating mechanisms within the execution stage operating handle according to some embodiments.

FIG. 5C is a perspective view of operating handle 402 enlarged to emphasize exemplary construction of some of the parts shown in FIG. 5A, including tensioning mechanism 502, external sheath retraction mechanism 504, cutter rotation mechanism 506, dilation balloon inflation port 508, and implant release mechanism actuator 510 according to some embodiments.

The component parts of tensioning mechanism 502 are shown in an exploded view in FIG. 5D. The construction of tensioning mechanism 502 is largely the same as that of planning stage device tensioning mechanism 302 illustrated in FIGS. 3E-3G, including a handle guide 512, a compression spring 514, a tube lock cylinder 516, and a lock knob 525, which are of the same construction as corresponding parts 332, 334, and 336, respectively. Tensioning mechanism 592 also includes a marker pointer 518, and tension is applied by pulling on operating handle 402 rather than by pull handle 330.

The distal end of spring 514 is restrained by a collar, half of which is formed in handle body 500 and shown at 522 in FIG. 5C, and the other half of which is formed in a complementary position in handle cover 490.

As in the case of the tensioning mechanism described in connection with planning stage device 300, tensioning mechanism 502 is used to apply a selected repeatable tension to catheter delivery tube 308. The applied tension is advantageously approximately the same as that applied to anchoring balloon delivery tube 308 during the planning stage so that the proximal markers 316 on delivery tube 308 can on used to locate dilation balloon 412 and cutter 416 properly during the execution stage. Thus, using the proximal markers 316 as a guide, handle 402 is locked to anchoring balloon shaft 308 at the position determined during the planning stage. In this connection, it should be recalled that the positions of the proximal and distal markers are correlated since the shaft length is fixed. The distance between every two correlated markers is the total distance between the blade and the end of the handle, which is always fixed.

FIG. 5E is a perspective view of marker pointer 518. This is comprised of a tubular body 524 having an internal passage 526 that receives shaft 524 of locking knob 525, and a pair of wings 528a and 528b with pointing elements 530a and 530b at their respective lower ends.

FIG. 5F is an enlarged perspective view showing the way that pointers 530a and 530b are used according to some embodiments of the invention. As illustrated, body 500 and cover 490 include cut out areas the form a channel 522 when the two external parts are fitted together within which lock knob shaft 524 slides when handle 402 is pulled proximally. A series of tension markers 523 are provided along the both sides of channel 522 which cooperate with pointer elements 530 to indicate the tension.

Other ways to help the surgeon apply the same tension during the execution stage as was applied during the planning stage are also possible within the scope of the invention. In an embodiment illustrated in FIG. 5G, tension markers 523 and pointers 530 are not needed to indicate the required execution stage tension. In this embodiment, a pressure sensing device 590 is connected between positioning catheter delivery tube 308 and a source of inflation fluid 592. Pressure sensor 590 is connected to a pressure recording and indicating device 594 which operates to record the pressure on anchoring balloon 306 as a result of tension applied during the planning phase and to provide a visual and/or aural indication when the same tension is applied during the execution stage.

This functionality may be better understood by recognizing that in both the planning and execution stages, when anchoring balloon is fully inflated, but no tension is being applied the pressure measured by sensor 590 is a fixed value $P_0$, for example, 50 mm Hg. When tension is applied, however, balloon 306 is pressurized to an increased pressure $\Delta P$ resulting from the tension force. Since it is desired for $\Delta P$ to be approximately the same in the planning and execution stages, pressure indicator 594 can be constructed to record the selected inflation pressure and $\Delta P$ during the planning stage, and to provide a visual indication and/or an aural indication such as a tone. The surgeon maintains the tension so that $\Delta P$ remains substantially constant throughout the execution stage.

Alternatively, pressure indicator 594 can include an adjustment mechanism to permit pre-selection of a desired tension. This can be indicated to the surgeon during both the planning and execution stages. It is to be expected that a suitable tension will vary from patient to patient. This can be determined visually at the beginning of the planning stage using the working channel optical unit.

To relieve the surgeon of the need to maintain the tension during the execution stage by hand in either of the embodiments described, an attachment may be provided on the surgical table to hold handle 402 in a fixed position after the tension has been applied.

The construction of an exemplary external sheath retraction mechanism 504 is shown in FIGS. 5H (a side view) and 5I (a distal end view). Mechanism 504 is comprised of a rack 532, a rack cylinder 534, control knobs 424, spur gear 536, a gear shaft 538, and plungers 540. Rack 532 is attached at its distal end 542 to rack cylinder 534 which is attached, for example, by laser welding or adhesive, on external sheath 404.

Control knobs 424 and spur gear 536 are mounted on gear shaft 538 so that counter-clockwise rotation of either knob will retract external sheath 404, i.e., proximally. A return spring 544 attached at one end to the handle body and at its other end to cylinder 534 applies tension to facilitate re-extension of the sheath (see also FIG. 5A).

Figure 5I:
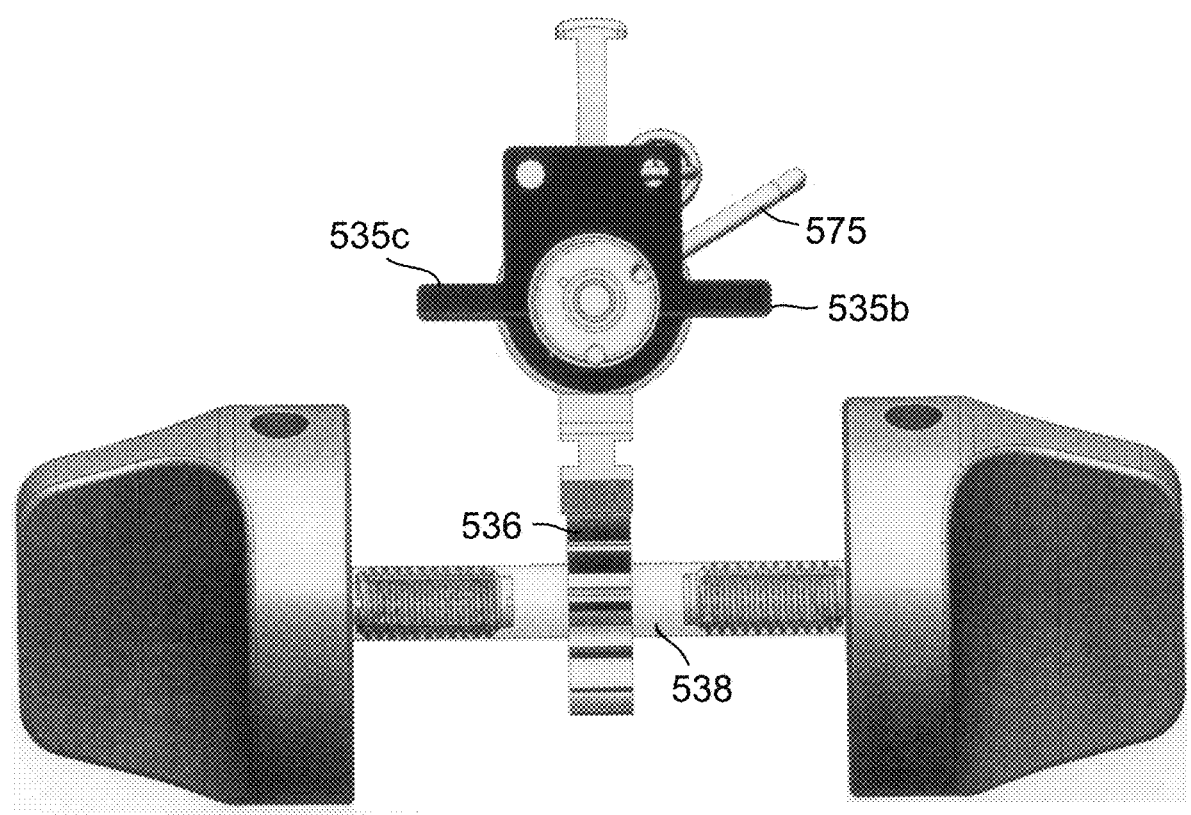
FIG. 5I is a proximal end elevation view of the sheath retraction mechanism shown in FIG. 5H.

Referring still to FIGS. 5H and 5I, it may be seen that that rack cylinder 534 includes a vertical projection 535a, and two sideward-extending projections 535b and 535c, Projection 535a extends outward in a slot 537 in the top of the body and side cover of operating handle 402 (see FIG. 5B) and serves as an indicator for the position of external sheath 402 while being retracted and extended. This allows the operator to know that the sheath has been fully retracted when indicator 535a is at the proximal end of its slot 537. Correspondingly, when sheath 404 is being re-extended, full extension is indicated when indicator 535a is at the distal end of slot 537.

Sideward projections 535b and 535c provide a mounting arrangement for cylinder 534 and for the proximal end of outer sheath 404. Projections 535b and 535c slide in dedicated slots in handle body 500 and cover 490 (not shown) as sheath 404 is retracted and extended. As will be appreciated, the distal end of the slot 537 also serves as a stopper for re-extension of the sheath.

For reference and orientation relative to FIGS. 4A and 4B, FIG. 5H also shows cutter delivery tube 420, implant release pin tube 575, and dilation balloon delivery tube 414.

The construction of an exemplary cutter rotation mechanism 506 is shown in FIG. 5A. Cutter rotation mechanism 506 is comprised of a gear segment 546 mounted on rotation trigger 428, a transmission gear arrangement comprising coaxially mounted spur gears 548 and 550, and a pair of bevel gears 552 and 554, the latter being mounted on dilation balloon delivery tube 414.

Pulling on trigger 428 causes dilation balloon inflation tube 414 (and attached cutter tube 420 and implant carrier tube 422) to rotate in the clockwise direction (relative to the proximal end).

Referring still to FIG. 5A, and also to FIG. 4D, it will be recalled that blade pusher wire 462 is connected to a source of power such as a diathermy machine or a piezoelectric transducer. In an exemplary embodiment, power cable 432 passes through operating handle 402 and is loosely coiled around dilation balloon tube 414 at 579

A return spring 536 is connected between handle body 500 and electrical wire 432 so that as the wire unwinds while the blade is rotating, tension is maintained on the wire.

Figure 5J:
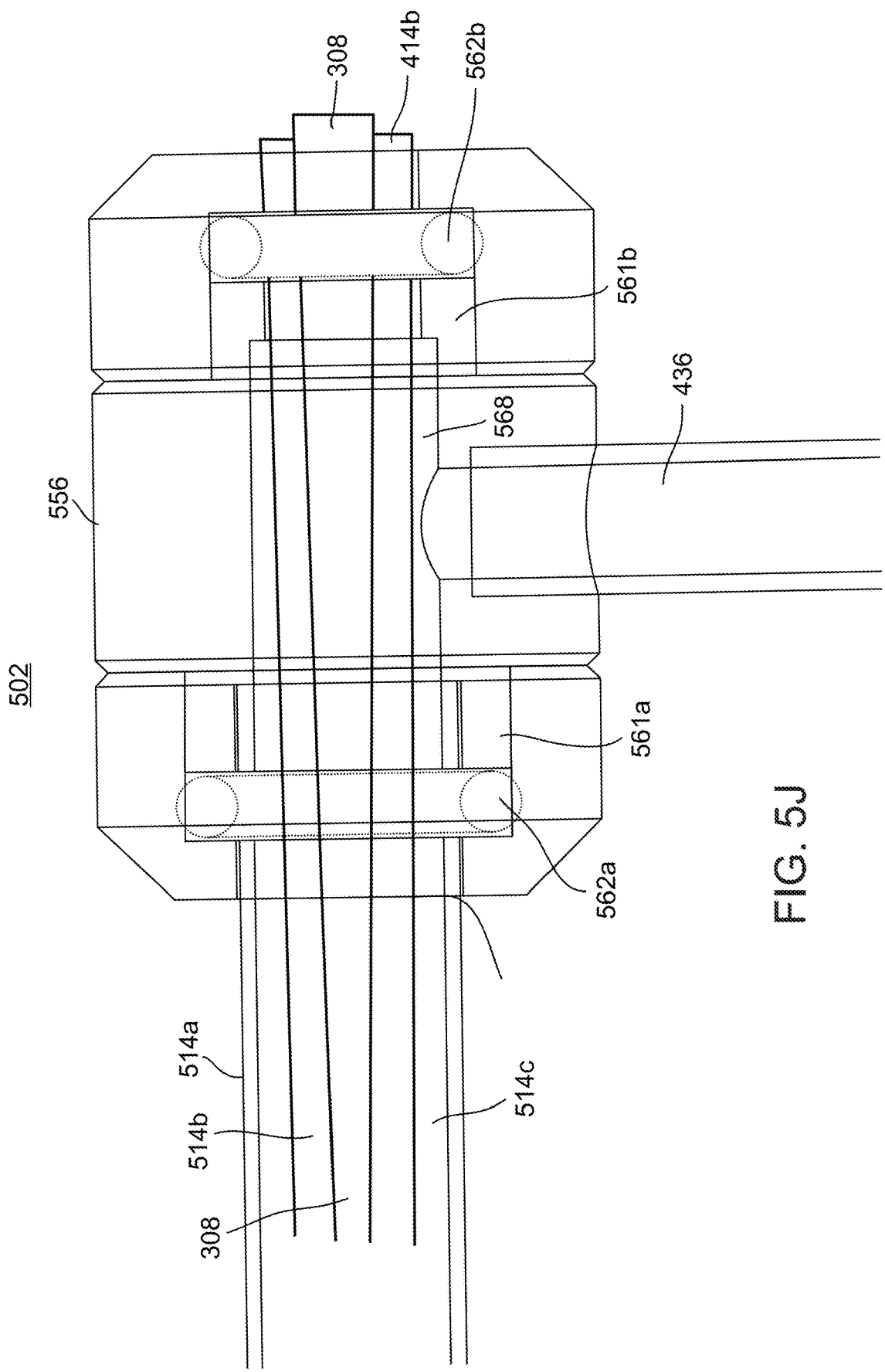
FIG. 5J is an enlarged side view of a dilation unit inflation port for a rotatable dilation unit inflation tube according to some embodiments.

As described in connection with FIG. 4B, dilation balloon inflation tube 414 is comprised of two concentric tube sections 414a and 414b partially welded at least near their respective distal ends (and optionally near their proximal ends as well) to provide an annular inflation fluid passage 414c through which balloon 412 is inflated. FIG. 5J illustrates the construction of an exemplary dilation balloon inflation port 508 in a side elevation with portions transparent to show internal parts. Inflation port 508 is comprised of a body 556, an internal tubular section 558 coupled to inflation tube 436, and end sections 560a and 560b. Within end section 560a is a fitting 561a that terminates in a fluid-tight (i.e., both gas and liquid tight) coupling element 562a. Similarly, within end section 560b is a fitting 561b that terminates in a fluid-tight coupling element 562b. Coupling element 562a is rotatably sealed around dilation balloon inflation tube outer section 414a which terminates inside body portion 558. Coupling element 562b is sealed around inflation tube inner section 414b which extends distally beyond coupling element 562b. This allows tube sections 414a and 414b to rotate within the respective seals without leakage of inflation fluid provided to annular passage 414c. As may also be seen in FIG. 5J, anchoring balloon inflation tube 308 passes through inner tube section 414b and is held in place by locking screw 426 comprised in tensioning mechanism 502 as described above (see FIGS. 5C and 5D). Consequently, no seal is needed around inflation tube 308.

Figure 5L:
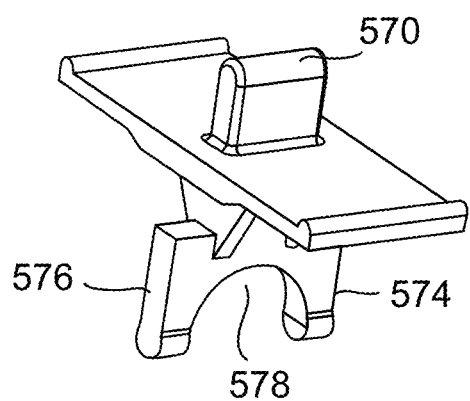
FIG. 5L is a perspective view of a pull handle comprised in the implant release trigger mechanism shown in FIG. 5L according to some embodiments.
Figure 5M:
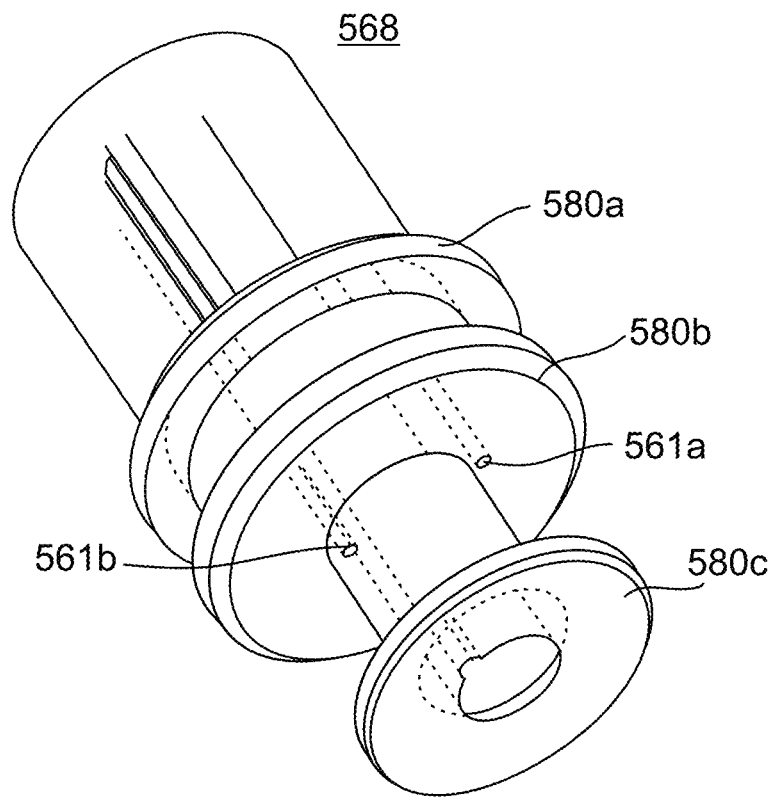
FIG. 5M is a side perspective view of a guide flange comprised in the mechanism shown in FIG. 5K according to some embodiments.

The construction of an exemplary implant release mechanism 510 (see FIGS. 5A and 5B) is shown in enlarged views in FIGS. 5K-5M. Implant release mechanism 510 is comprised of a release trigger 566, a release flange 568, both formed of a suitable material, for example, ABS, stainless steel, polycarbonate. Implant release mechanism also includes pin 468, the latter being located within tube 475 (see FIGS. 4B and 4C). Release trigger 566 is shown in an enlarged perspective view in FIG. 5L. Release flange 568 and carrier tube 475 are shown in an enlarged perspective view in FIG. 5M.

Release trigger 566 is comprised of an upstanding finger pull 570 mounted on a slide plate 572 and a body portion 574 terminating in a pair of downwardly depending fingers 576 forming an arcuate opening 578 that fits between flange rings 580a and 580b on release flange 568. An additional ring 580c cooperates with ring 580b to serve as a spool around which power wire coil 579 is wound, as previously noted.

Implant release pin 468 and cutter pusher wire 462 extend through release flange ring 580b and are attached to it, for example, by a suitable adhesive at 561a and 561b, respectively. Power connector wire 432 is attached to blade pusher wire 462 at 561b.

Alternatively, in some embodiments, release pin 468 and cutter pusher wire 462 can be attached to separate flange rings. In other embodiments, pusher wire 462 is not connected to the release flange.

Release flange 568 is slidable on dilation unit delivery tube 414, on cutter delivery tube 420 and on implant release tube 475 so that pin 468 and cutter blade 418 can be pulled proximally by trigger 566 to decouple the projecting end 474 of implant release pin 468 from the implant (see FIGS. 4B and 4C) and to retract cutter blade 418. Retracting both pin projection 474 and cutter blade 418 can be advantageous in some cases since it allows cutter blade 418 to be pulled proximally at the same time the implant is released to help assure safe retraction of the entire delivery system.

Referring again to FIG. 5B, it may be seen that finger pull 570 extends out of a slot 571 defined by cut out portions of handle body 500 and handle cover 490 for convenient access.

Figure 5N:
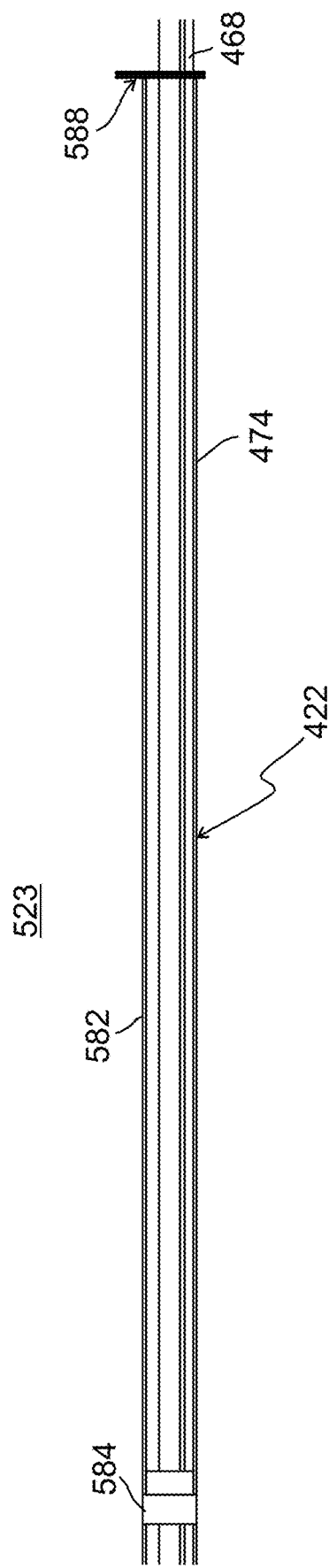
FIG. 5N is side elevation of an implant pusher for the execution stage device according to some embodiments.
Figure 50:
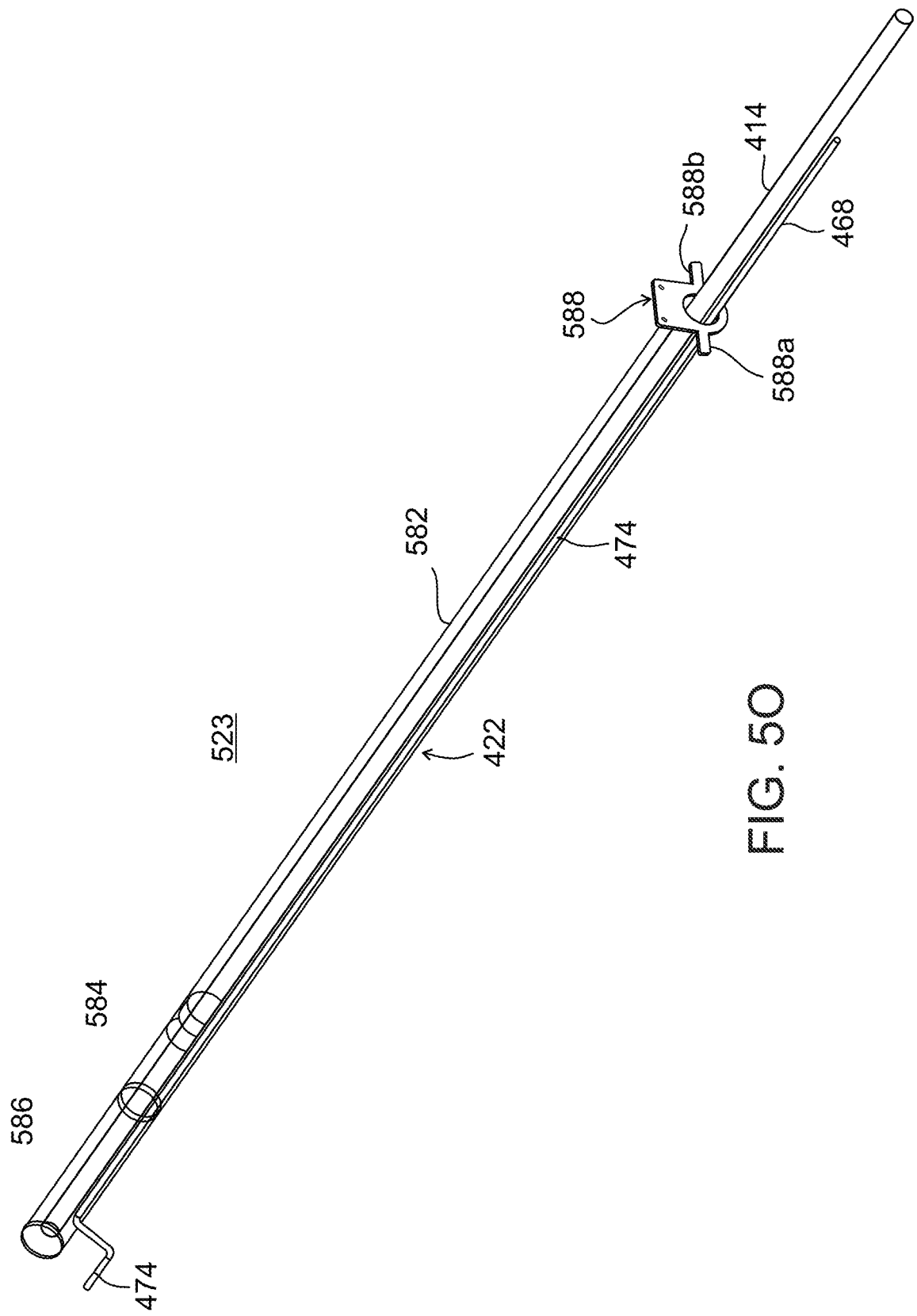

FIGS. 5N and 5O show side and perspective views, respectively, of an exemplary implant delivery pusher mechanism 523 according to some embodiments of the invention. Pusher mechanism 523 helps assure ejection of the implants from external sheath 404 (see FIG. 5C). Since the implant is delivered rolled up inside sheath 404, it presses against the inside of the sheath, and the resulting friction impedes the release of the implant when the outer sheath is retracted. Pusher mechanism 523 applies a distally directed force on the implant which helps prevents it from remaining within outer sheath 404 when the sheath is retracted.

Implant pusher assembly 523 in the illustrated exemplary embodiment is comprised of a pusher tube 582, an implant pusher 584 that engages an implant 586 rolled up for delivery shown in FIG. 5O, and a pusher flange 588, all of which are delivered to the implantation site within outer sheath 404 as previously explained. Implant pusher 584 is attached at its proximal end to the distal part of the pusher tube 582 and is the part that actually engages the implant to push it out of sheath 404.

Referring to FIG. 5O, pusher flange 588 includes two sideward projections 588a and 588b that are slidably mounted in tracks on the handle body and the cover, and which provide support for the proximal end of the pusher mechanism.

Representative Method Embodiments

Figure 6A:
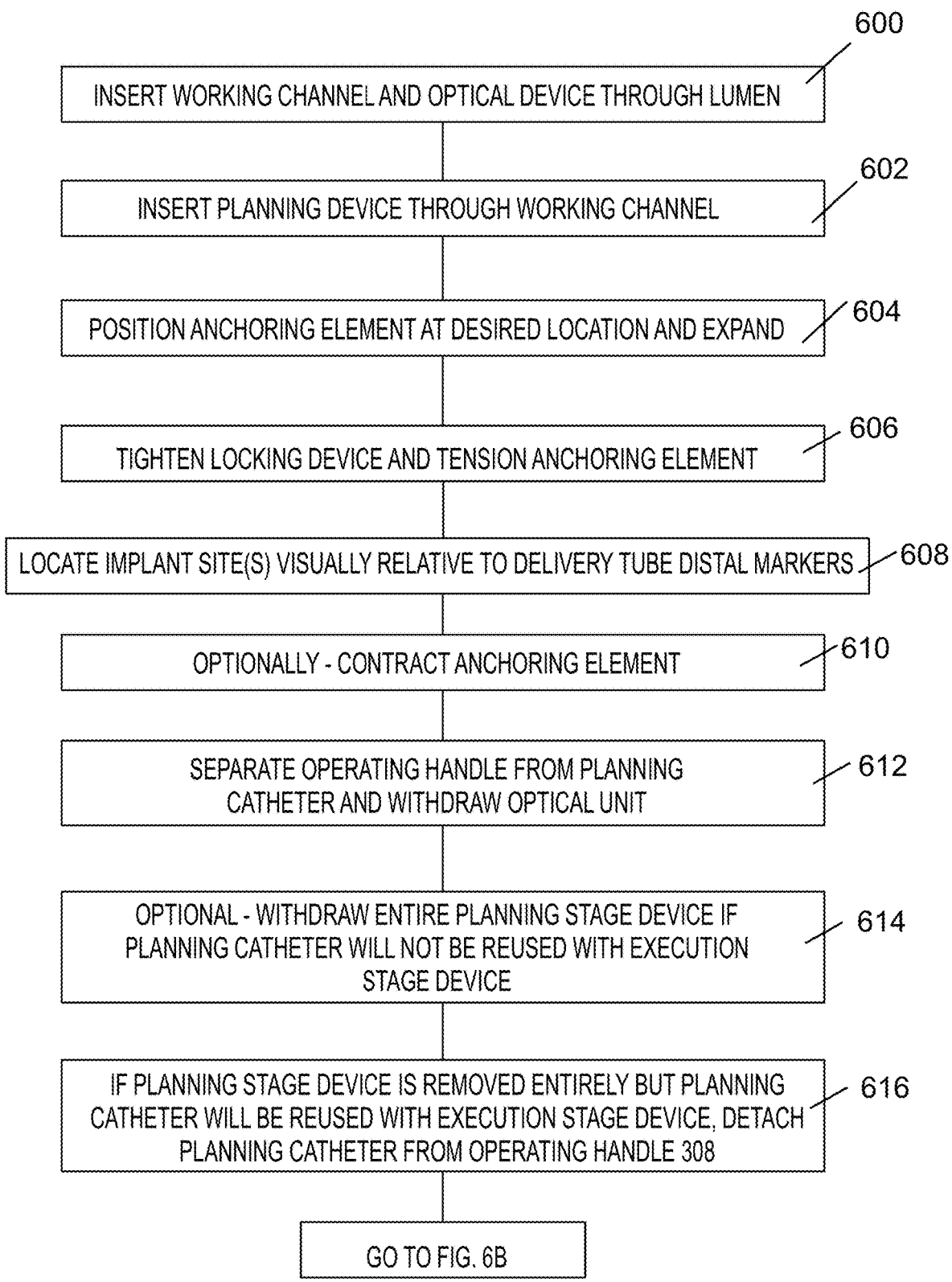
FIGS. 6A and 6B are a flow chart showing the elements of an exemplary method of treating a constricted lumen according to some embodiments.
Figure 6B:
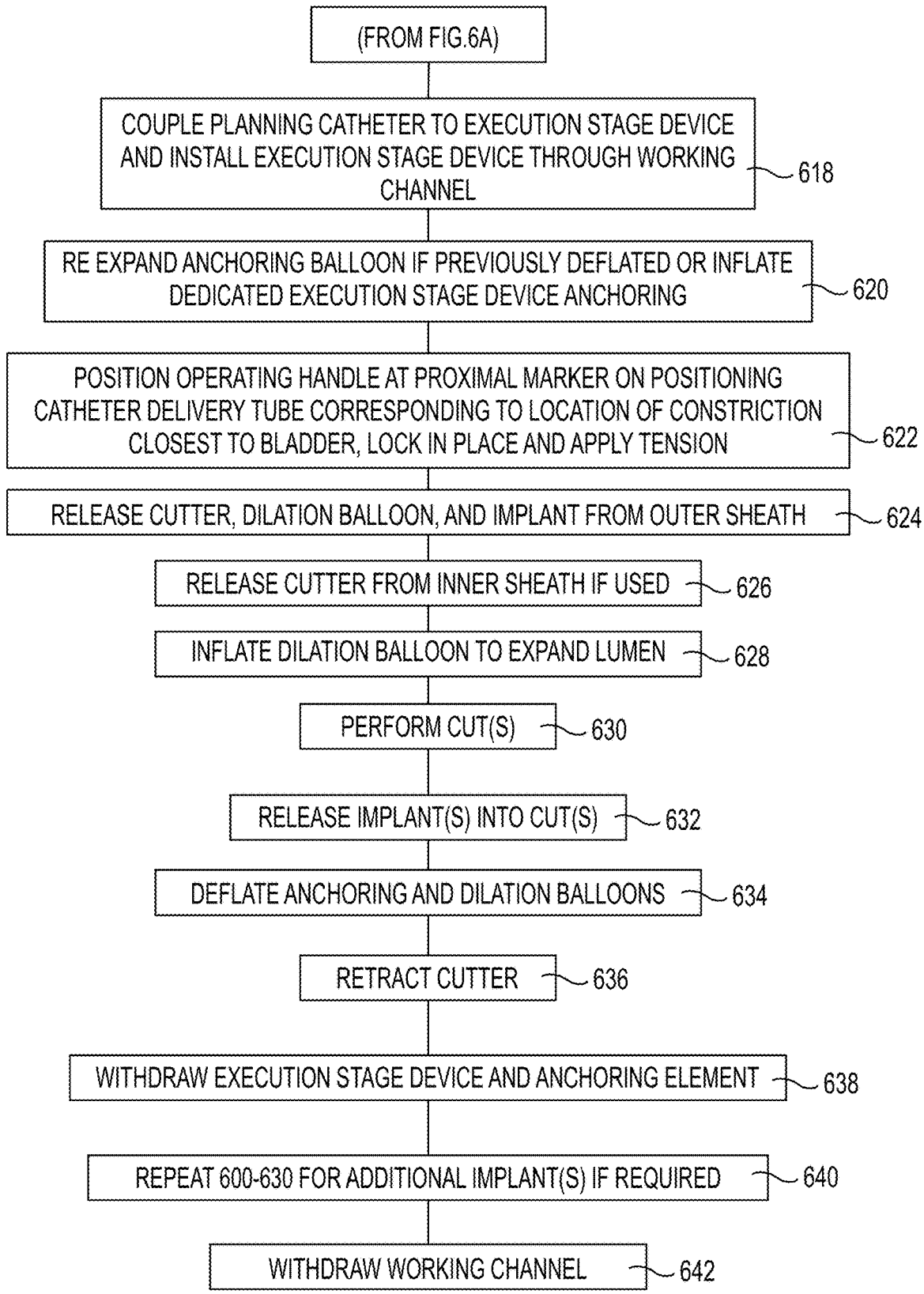

FIGS. 6A and 6B are a flow chart that illustrates an exemplary method of treating a constricted lumen such as a urethra using exemplary planning and execution stage devices 300 and 400 according to the two-stage methodology as well as some variations in the method according to different embodiments of the invention.

Preliminarily, is should be noted that the parts of the system described herein may be made available in several different combinations and/or configurations. For example, a kit may be provided comprising one planning stage operating handle and a plurality of planning catheters. In such an arrangement, the operating handle should be constructed of materials that can be sterilized for reuse.

In some embodiments, the execution stage device may be provided in a kit including a single operating handle and a plurality of deployment sub-units each comprised of a dilation device, one or more cutters, one or more implants, and an implant release mechanism. As will be understood, in such an arrangement, the execution stage operating handle will be designed for convenient coupling to the deployment sub-unit. Various options for coupling the two units are possible within the scope of the invention.

Bearing the foregoing in mind, referring to FIG. 6A, at 600, in preparation for the procedure, a device, for example, a conventional cystoscope or resectoscope in the case of treatment of a urethra is inserted through the lumen to provide a working channel. The device will usually include an optical unit suitable for viewing the interior of the lumen.

At 602, the planning device 300 is inserted through the working channel, At 604, the anchoring element, for example, balloon 306 or other suitable anchoring element is positioned and expanded to prevent movement of the positioning device. As noted above, in the case of treatment of BPH, the anchoring element may be positioned in the neck of the bladder as observed using the previously inserted optical unit.

At 606, locking element knob 338 is tightened to unite the planning catheter to the operating handle, and tension is applied to firmly seat the anchoring element. In this connection, it should be understood that in some embodiments designed for treatment of lumens other that a urethra, it may not be necessary to apply tension to the anchoring element. In embodiments specifically dedicated to such applications, it may be possible to omit the tensioning mechanism from the planning device operating handle and also from the execution device operating handle.

At 608, the optical device is used to identify one or more implant-deployment locations using the distal markers 314 on delivery tube 308 as a reference.

Optionally, in some embodiments, at 610, where necessary to permit withdrawal of the optical unit, anchoring element 306 is contracted, and at 612 operating handle 302 is separated from planning catheter 304 by loosening knob 338 sufficiently to disconnect delivery tube 308 from handle guide 332.

At 614, the optical device is withdrawn through the working channel. In those embodiments in which the planning catheter is left in place, and does not need to be contracted to permit withdrawal of the optical unit, 610 is omitted, and the process goes directly from 608 to 612.

As another option, at 616, in embodiments in which execution stage device 400 includes a dedicated planning catheter, planning stage catheter 304 is withdrawn entirely. In such embodiments, anchoring element 306 is contracted and planning stage device 300 is withdrawn through the working channel by pulling handle 302 proximally without loosening locking screw knob 338. Since delivery tube 308 remains connected to handle guide 332 but anchoring balloon 306 has been deflated, the positioning catheter can easily be withdrawn through the working channel.

Referring now to FIG. 6B, at 618, if planning catheter 304 is to be reused with the execution stage device 400, it will typically be left in place in the lumen (whether contracted or left expanded) and is coupled to execution stage operating handle 400 by insertion of its proximal end through inner tube 414b of dilation device delivery tube 414.

At 620, if the planning stage planning catheter is reused but has been contracted, it is re-expanded. In the embodiments in which execution stage device 400 includes its own positioning catheter, the dedicated anchoring element of execution device 400 is expanded.

At 622, the planning catheter is positioned at the proximal marker corresponding to the first implant deployment location, locked in place, and tension is applied, if applicable to treatment of a particular lumen.

At 624, outer sheath 402 is retracted, and the cutter, the dilation balloon, the implant, and the implant release mechanism are exposed. At 626, if the cutter nit is carried in a separate inner sheath, is also pushed out of the inner sheath. Pusher assembly 523 is used to assure that the implant(s) are released when the outer sheath is retracted.

At 628, the dilation balloon is inflated to expand the lumen. At 630, the cutter is operated to form the cut for receiving the implant. At 632, the implant is released for deployment in the cut.

At 634 the dilation balloon and the anchoring balloon are deflated.

At 636 the cutter is retracted into its delivery tube or into the outer sheath (in embodiments that do not employ a separate delivery tube), and at 638, the execution unit and the anchoring balloon and its delivery tube are withdrawn through the working channel.

At 640, 620-638 are repeated for additional implant(s) if required and are not deployed simultaneously.

Finally, at 642, the working channel is withdrawn.

According to some embodiments, it may be advantageous under certain circumstances, to remove the implant(s) after a period of time, or to form them of a biodegradable material. This may be desirable, for example to reduce inherent risks of permanent implantation of any structure in the body. It has been found that even temporary presence of an implant inside an incision force the tissue surrounding the lumen to recover in a reshaped way—actually distorting the original shape of the tissue to maintain the patency of the lumen even after implant removal. The resulting "scar" associated with the implantation has negligible effect.

Figure 7A:
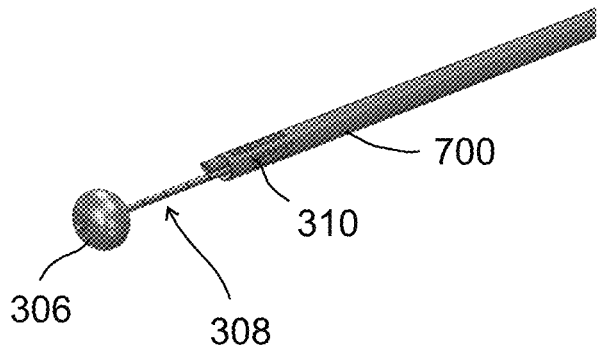
FIGS. 7A, 7B, 7C, and 7D are illustrations of apparatus in configurations corresponding to several elements of the method of FIGS. 6A and 6B.

FIG. 7A shows the planning catheter 308 extending out of the distal end 700 of a cystoscope 702 and extended out of its sheath 310 (See FIG. 3A) with anchoring balloon 306 inflated through delivery tube 308, as it would appear at the completion of method element 604.

Figure 7B:
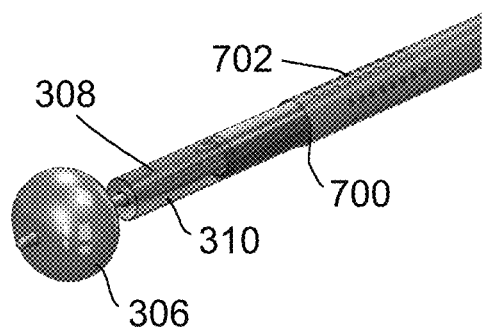

FIG. 7B shows the configuration of the distal end of execution device 400 (See FIG. 4A) installed over anchoring balloon delivery tube 308 with outer sheath 402 in its delivery configuration extending out of the distal end 700 of cystoscope 702, and with anchoring balloon 306 inflated. This is the situation after method element 614.

Figure 7C:
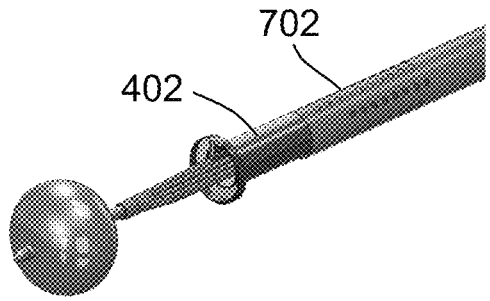

FIG. 7C shows the distal end of execution device 400 after retraction of outer sheath 402 with dilation balloon 406, cutter unit 410, and implant 414 exposed but before inflation of balloon 406 after completion of method element 624 (and 626 if an inner sheath is employed).

Figure 7D:
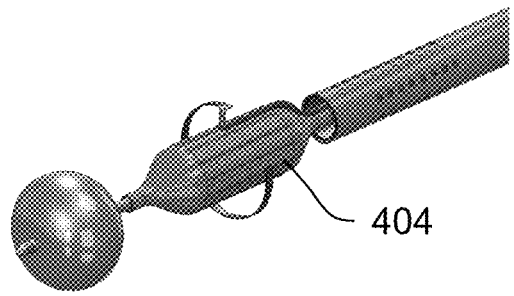

FIG. 7D shows dilation balloon 406 inflated, but before the cut has been formed in the prostate, corresponding to method element 628.

Figure 8:
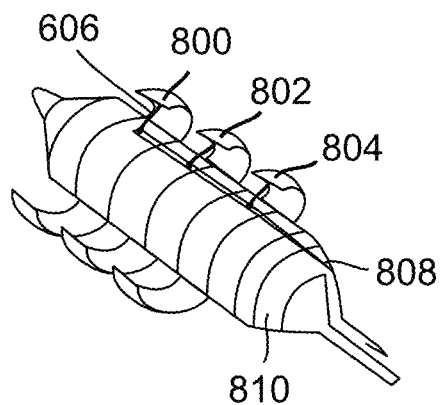
FIG. 8 is a pictorial schematic illustration of an arrangement for simultaneous deployment of several implants.

FIG. 8 shows in highly schematic form one option for deployment of multiple implants according to some embodiments. Here, the execution device carries three implants 800, 802, and 804 and three cutters 806 carried by a delivery tube indicated schematically at 808 and mounted on a dilation balloon 810. In this situation, cuts would be performed for all three implants simultaneously (at 630) released simultaneously (at 632) a release mechanism (not shown for clarity) and no repetition (at 640).

Although FIG. 8 illustrates three implants, a larger number, for example, four, five or even more may be provided. In some embodiments the spacing between the implants is fixed. In some embodiments the spacing may be adjusted before delivery to the treatment site according to observations made during the planning stage.

According to another option, several implants may be deployed successively using separate execution devices. In this case, method elements are repeated as many times are necessary to deploy all the required implants (at 640). Typically, a separate execution device would be used for each successively deployed implant. Optionally, the same operating handle is used each time.

General Comments

It will be appreciated that other constructions for the functional features of operating handles 302 and 402 are also within the scope of embodiments of the invention. For example, the locking elements for the tensioning mechanisms can comprise lever-operated or twistable cam locks or over-centering mechanisms to engage the locking cylinder. Likewise, constructions other than those shown and described for the operating features of the execution stage operating handle are also possible within the scope of the invention.

Although the invention has been described in conjunction with specific embodiments thereof, it is evident that many alternatives, modifications, and variations will be apparent to those skilled in the art. Accordingly, it is intended to embrace all such alternatives, modifications, and variations that fall within the spirit and broad scope of the appended claims.

Specific features comprised in a described embodiment are to be considered as exemplary of that embodiment. The described embodiment should not necessarily be construed to require the feature and the feature should be regarded as suitable for inclusion in other embodiments unless otherwise clearly indicated.

The terms "comprises", "comprising", "includes", "including", "having" and their conjugates mean "including but not limited to". This also encompasses the terms "consisting of" and "consisting essentially of".

As used herein, the singular form "a", "an" and "the" include plural references unless the context clearly dictates otherwise. For example, the term "an element" or "at least one element" may include a plurality of elements. The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein the term "method" refers to manners, means, techniques and procedures for accomplishing a given task including, but not limited to, those manners, means, techniques and procedures either known to, or readily developed from known manners, means, techniques and procedures by practitioners of the relevant technological arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It should be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention.

Certain features described in the context of various embodiments are not to be considered essential features of those embodiments, unless the embodiment is inoperative without those elements.

All publications, patents, and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A method for treatment of a urethra that is constricted due to benign prostatic hyperplasia (BPH), the method comprising:
   using a positioning device, determining a location of the area of the urethra that is constricted and is to be treated;
   inserting an execution device into the urethra,
      the execution device including a dilation balloon, a cutter disposed outside the outer surface of the dilation balloon, an implant carrier, and an implant that is housed at least partially by the implant carrier,
      the implant carrier and the implant being disposed outside the outer surface of the dilation balloon at an axial location along the dilation balloon that is aligned with the cutter;
   delivering the implant to the area of the urethra, using the execution device;
   dilating the area of the urethra, by expanding the dilation balloon;
   subsequent to dilating the area of the urethra, forming a cut in an inner surface of the urethra at the area of the urethra, using the cutter; and
   subsequent to forming the cut in the inner surface of the urethra at the area of the urethra, releasing the implant from the implant carrier into the cut, to thereby maintain the area of the urethra in a dilated state.

2. The method according to claim 1, wherein the execution device further includes a cutter rotation mechanism, and wherein forming the cut in the inner surface of the urethra at the area of the urethra comprises rotating the blade of the cutter around the inner surface of the urethra to form a circular cut in the inner surface of the urethra as the cutter is rotated.

3. The method according to claim 1, wherein releasing the implant from the implant carrier into the cut comprises releasing the entire implant from the implant carrier into the cut within the inner surface of the urethra.

4. The method according to claim 1, wherein forming the cut the inner surface of the urethra at the area of the urethra comprises forming the cut the inner surface of the urethra at the area of the urethra as a single continuous circular cut in the inner surface of the urethra at the area of the urethra.

5. The method according to claim 1, wherein the implant carrier is configured to engage releasably with the implant, wherein the execution device includes a release unit configured to separate the implant from the implant carrier, and wherein the method further includes separating the implant from the implant carrier using the release unit.

6. The method according to claim 1, wherein the implant is shaped to define a substantially C-shaped implant, and wherein releasing the implant into the cut comprises releasing the substantially C-shaped implant such that an open portion of the C-shaped implant faces a rectum wall to thereby maintain the urethra in the dilated state.

7. The method according to claim 1, further comprising closing the cut in the inner surface of the urethra subsequent to releasing the implant into the cut by application of an adhesive, or by a clamp, or by a suture.

8. The method according to claim 1, wherein the execution device includes two or more implants, and wherein:
   delivering the implant to the area of the urethra comprises delivering the two or more implants to the area of the urethra;
   forming the cut in the inner surface of the urethra at the area of the urethra comprising forming two or more cuts in the inner surface of the urethra simultaneously; and
   releasing the implant from the implant carrier into the cut comprises releasing the two or more implants from the implant carrier simultaneously into the two or more cuts within the inner surface of the urethra.

9. The method according to claim 1, wherein forming the cut in the inner surface of the urethra at the area of the urethra further comprises connecting the cutter to a diathermy machine or a piezoelectric transducer to provide a source of electrical or electromechanical energy and rotating the cutter around the inner surface of the urethra.

10. The method according to claim 1, further comprising removing the implant after a predetermined time.

11. The method according to claim 1, wherein the implant is formed of a material that is biodegradable, and wherein releasing the implant from the implant carrier into the cut comprises releasing the biodegradable implant from the implant carrier into the cut.

12. The method according to claim 1, further comprising connecting the positioning device to the execution device for use during the treatment.

13. The method according to claim 1, wherein determining the location of the constricted area of the urethra that is to be treated, comprises:
   transurethrally inserting the positioning device into the urethra, the positioning device including an anchor and an anchor delivery shaft;
   anchoring the positioning device in a neck of a bladder;
   inserting an optical device into the urethra; and
   visually identifying the area of the urethra that is constricted and is to be treated.

14. The method according to claim 13, wherein visually identifying the area of the urethra that is constricted and is to be treated comprises visually identifying the area of the urethra that is constricted and is to be treated relative to spaced markings extending proximally on the anchor delivery shaft from adjacent to the anchor.

15. The method according to claim 13, wherein the anchor includes an anchor balloon, and wherein the method includes inflating the anchor balloon and the dilation balloon using a liquid as an inflation fluid.

* * * * *